United States Patent
Grayfer et al.

(10) Patent No.: US 7,430,893 B2
(45) Date of Patent: Oct. 7, 2008

(54) SYSTEMS AND METHODS FOR DETECTING CONTAMINANTS

(75) Inventors: Anatoly Grayfer, Newton, MA (US); Jürgen Michael Lobert, Franklin, MA (US); William Goodwin, Medway, MA (US); Frank Vincent Belanger, Webster, MA (US); John E. Sergi, Franklin, MA (US); Mark C. Phelps, Attleboro, MA (US)

(73) Assignee: Entegris, Inc., Chaska, MN (US)

( * ) Notice: Subject to any disclaimer, the term of this patent is extended or adjusted under 35 U.S.C. 154(b) by 0 days.

(21) Appl. No.: 11/001,669

(22) Filed: Dec. 1, 2004

(65) Prior Publication Data
US 2005/0183490 A1 Aug. 25, 2005

Related U.S. Application Data

(63) Continuation-in-part of application No. 10/933,692, filed on Sep. 2, 2004.

(60) Provisional application No. 60/526,862, filed on Dec. 3, 2003.

(51) Int. Cl.
*G01N 1/22* (2006.01)

(52) U.S. Cl. .................. 73/23.2; 73/28.01; 73/28.04; 73/31.02; 73/31.03; 73/31.05

(58) Field of Classification Search .............. 73/23.2, 73/23.22, 28.01, 28.04, 31.01, 31.02, 31.03, 73/31.05
See application file for complete search history.

(56) References Cited

U.S. PATENT DOCUMENTS

| | | | | |
|---|---|---|---|---|
| 3,881,359 | A * | 5/1975 | Culbertson ............... | 73/863.12 |
| 4,686,848 | A * | 8/1987 | Casselberry et al. .......... | 73/38 |
| 5,574,230 | A | 11/1996 | Baugh | |
| 5,856,198 | A | 1/1999 | Joffe et al. | |
| 6,085,576 | A * | 7/2000 | Sunshine et al. .......... | 73/29.01 |
| 6,096,267 | A | 8/2000 | Kishkovich et al. | |
| 6,295,864 | B1 * | 10/2001 | You et al. ................. | 73/53.01 |
| 6,422,061 | B1 * | 7/2002 | Sunshine et al. .......... | 73/29.01 |
| 6,703,241 | B1 * | 3/2004 | Sunshine et al. .............. | 436/8 |
| 6,779,411 | B1 * | 8/2004 | Spurgeon ................. | 73/863.23 |
| 2002/0178923 | A1 | 12/2002 | Kishkovich et al. | |
| 2003/0068834 | A1 | 4/2003 | Kishkovich et al. | |
| 2005/0045039 | A1 | 3/2005 | Shellhammer et al. | |

* cited by examiner

*Primary Examiner*—Daniel S Larkin
(74) *Attorney, Agent, or Firm*—Hamilton, Brook, Smith & Reynolds, P.C.

(57) ABSTRACT

The present invention relates to a system and method for sampling a gas flow to measure one or more contaminants within a semiconductor processing tool. The system includes a portable unit containing one or more dry traps, Tenax traps and, if desired, wet impingers. The unit is coupled to a gas flow in a clean room and the dry traps, Tenax traps and wet impingers measure contaminants contained in the gas supply for a determined sampling interval. When the sampling interval is done, the unit is sent to an analysis facility for processing.

38 Claims, 35 Drawing Sheets

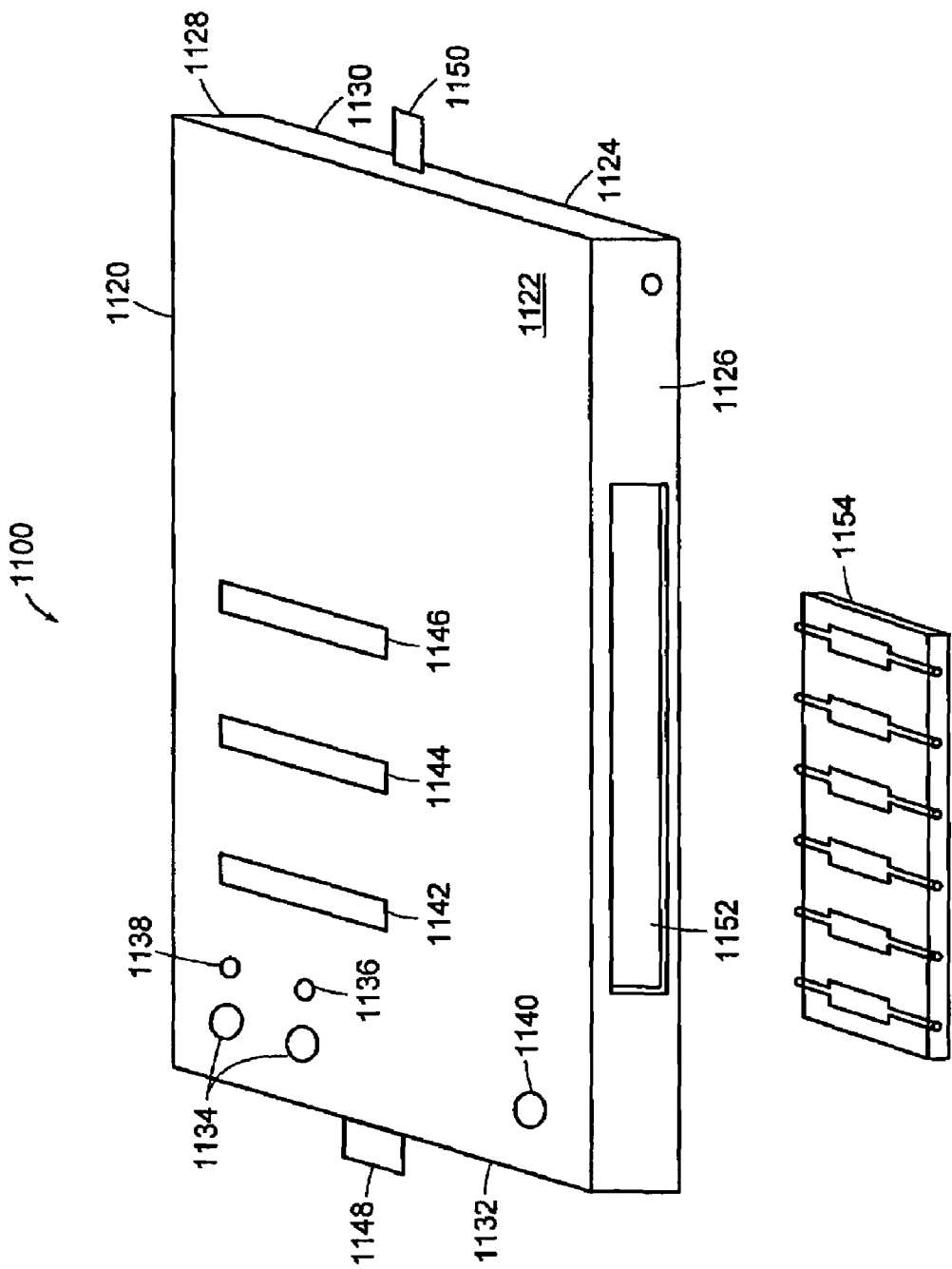

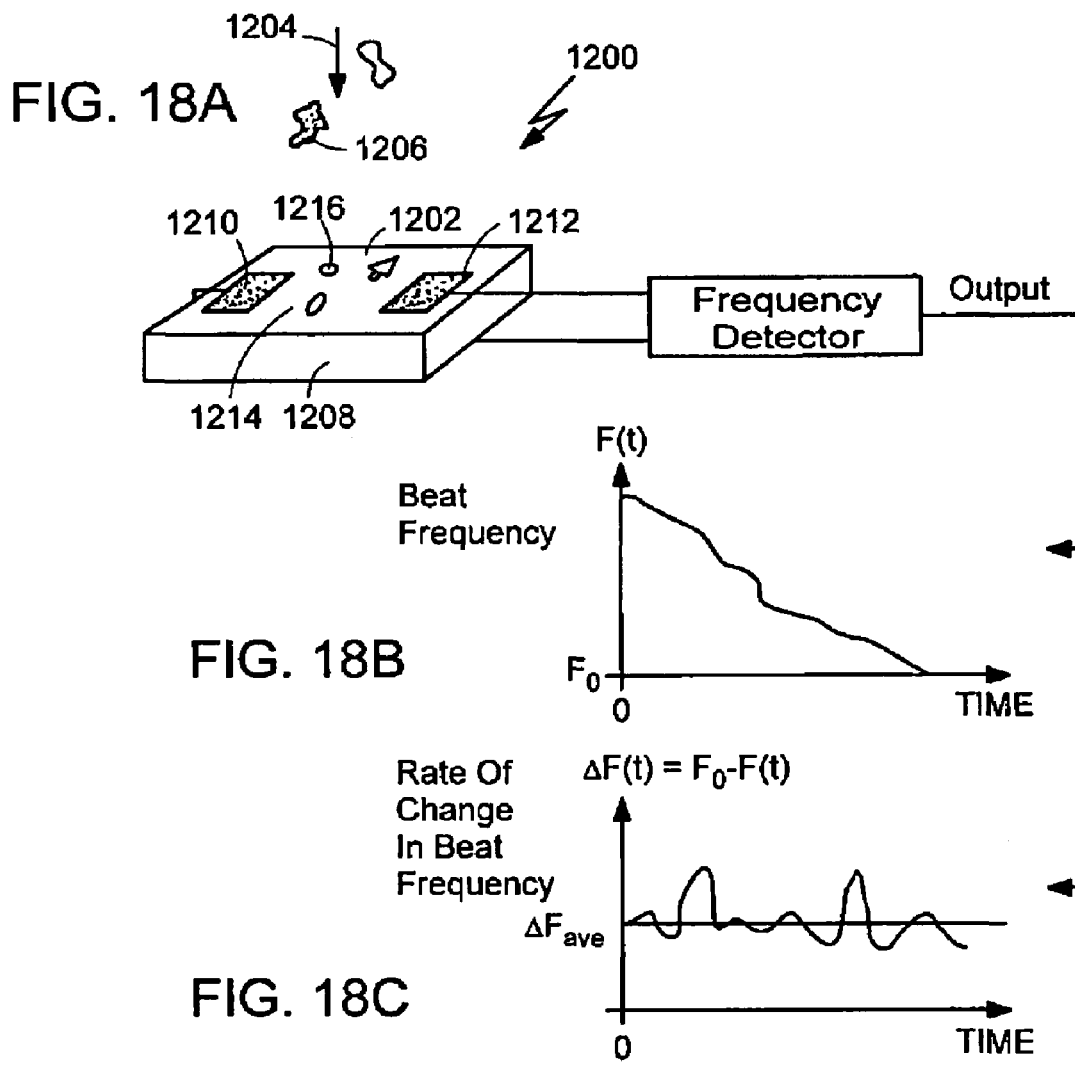

SYSTEMS AND METHODS FOR DETECTING CONTAMINANTS

CROSS REFERENCES TO RELATED APPLICATIONS

This patent application claims the benefit of U.S. provisional patent application 60/526,862 filed on Dec. 3, 2003, and is a continuation in-part of U.S. application Ser. No. 10/933,692 filed Sep. 2, 2004, the entire contents of these applications being incorporated herein by reference.

BACKGROUND OF THE INVENTION

Semiconductor manufacturers continue to measure and control the level of contamination in the processing environment, especially during the critical steps of the photolithography processes. The typical means of determining the quality and quantity of contamination in gas samples in cleanroom manufacturing environments involves sampling air and purge gases, such as, for example, filtered and unfiltered air, clean dry air, and nitrogen. One of the most common base contaminants in the air worldwide is ammonia. Within a semiconductor fabrication facility ammonia commonly arises from wet benches, chemical vapor deposition (CVD), cleaners, $Si_3N_4$ and TiN deposition, and people. And, outside the semiconductor fabrication facility, farms, fertilizer and sewers are major sources of ammonia.

Contaminant measurement systems used in semiconductor environments are typically of the continuous, or semi-continuous, sampling variety or of the fixed sampling interval variety. A continuous or semi-continuous sampling system is installed in a cleanroom and operates in a substantially ON state whenever the facility is operating. Continuous and semi-continuous sampling systems are typically equipped with measurement and analysis systems for providing data on contaminant levels within the cleanroom. As such, continuous and semi-continuous sampling systems do not require removal from a cleanroom in order for an operator to obtain data regarding contaminant levels within the cleanroom environment. Since continuous and semi-continuous sampling systems produce results on site, they are often large, complex and expensive to acquire, operate and maintain. In addition, these systems require periodic calibrations to ensure that they operate properly in the environment. In contrast, samplers of the fixed interval variety are often portable and inexpensive since they only sample gases within a cleanroom. Fixed sampling interval devices are removed from the cleanroom for analysis of contaminants contained therein. Analysis can be performed by an end user of the devices or the sampling devices can be sent offsite for analysis. Fixed interval sampling devices are attractive to end users because they are relatively simple to operate; however, prior art fixed interval sampling devices have shortcomings.

For example, one traditional sampling approach for determining the concentration of cleanroom contaminants, especially ammonia, using fixed interval sampling devices has been through the use of wet impingers. These wet impinging approaches have certain drawbacks including accidental spillage of the scrubbing media (typically, deionized (DI) water or a DI water solution), accidental inversions of the impinger, and limits to sampling time (thereby imposing limits on the lower-detection-limit of the approach) due to natural evaporation of scrubbing media (DI water). In addition, wet impinger systems frequently require installation of the impinger by a highly trained technician. Another shortcoming associated with wet systems is that an end user typically has to wait more than a week to receive analysis results after sending the wet impinger system to an analysis facility. Furthermore, wet impinger systems can be prone to bacterial contamination of the liquid scrubbing media and wet impinger vials are often made of fragile glass or quartz making them prone to breakage during shipment. Consequently, there is an ongoing need for improvements in systems and methods for the measurement of contamination of gases used for industrial processes using fixed interval sampling devices that do not require wet impinger based sampling.

SUMMARY OF THE INVENTION

The present invention relates generally to systems and methods for obtaining a sample from a gas to measure one or more contaminants therein. In various embodiments, the present invention provides systems and methods for air sampling that facilitate reducing or eliminating the drawbacks associated with traditional wet impinger approaches to sampling.

In one aspect, the present invention provides a sampler where the collection material is a dry media. Accordingly, such dry samplers are liquid free avoiding the problems associated with liquid spillage and liquid evaporation inherent to wet impingers.

The systems and methods of the present invention are of particular use in the measurement of contaminants in gases used in the semiconductor industry. For example, filters used in the removal of contaminants in gases used in photolithography tools must be replaced on a regular basis to avoid contamination of the tool environment and degradation of semiconductor wafers being manufactured with the tool. By sampling the air circulated within the tool, data can be acquired to determine the need for filter replacement on a regular basis. The systems and methods described herein can be used to measure air or other gases circulating within lithography exposure tools and or tracks and can be used to measure filter performance upstream, downstream or interstack (between or within filter elements), or they can be used to measure clean dry air (CDA) nitrogen ($N_2$) or other purge gases offgassing issues, or ambient conditions.

A preferred embodiment of the invention employs either passive or active sampling in which one or more sampling elements or pads are used to remove contaminants from a gas in contact with the sampling elements or pads.

In various embodiments, the present invention provides a dry sampler for ammonia with a lower detection limit (LDL) in the range between about 0.02 ppbV and 0.1 ppbV at a signal to noise ratio of at least about two and depending on the duration of the sampling.

In various embodiments, the present invention provides a dry sampler having one or more of a low ammonia background and detection limit of 0.1 ppbV for a four hour sampling time that corresponds to a 240 L collected volume; a low pressure drop across the dry sampler to enable, for example, use of current hand-held pumps for active sampling system configurations; high capture efficiency for ammonia.

A preferred embodiment of the invention includes a sampling system having a plurality of sampling or collection media to provide redundancy and/or to collect separate samples of different contaminants. For example, a first trap collects one or more bases, a second trap collects acidic materials and a third trap collects organic materials. The different samplers or traps are contained in a single housing with inlet and outlet ports for the gas being sampled. The samplers can be a combination of wet and dry traps, or all contaminants can be collected using a plurality of dry traps.

In a preferred embodiment of the invention, the sampling elements can include a Tenax™ trap to collect high molecular weight (high boiling point) organic compounds, a Tenax™ trap for the collection of low-molecular weight (low boiling point) organic compounds. One or more wet impinger filled with de-ionized water can be used for the collection or inorganic compounds (acids, bases and their precursors). Dry sampling elements can also be used for the measurement of inorganic compounds (e.g. acids, bases and their precursors).

A manifold is used to deliver gas samples through each of the traps and can include manual or automated valves to control fluid flow through the system. Control electronics are located within the housing to automate system operation and record performance data.

Analysis of the samples can be conducted using gas chromatography or mass spectrometry for organics and ion chromatography for acids and bases.

The foregoing and other features and advantages of the systems and methods for air sampling provided by various embodiments of the present invention will be apparent from the following more particular description of preferred embodiments as illustrated in the accompanying drawings in which like reference characters refer to the same parts throughout the different views.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 17B illustrates a handheld embodiment of a gas sampling system;

FIG. 18A illustrates a detector for use in monitoring contaminants in a gas supply;

FIGS. 18B and 18C illustrate the beat frequency and rate of change thereof for the detector of FIG. 18A, respectively;

DETAILED DESCRIPTION OF THE INVENTION

Figure 1:
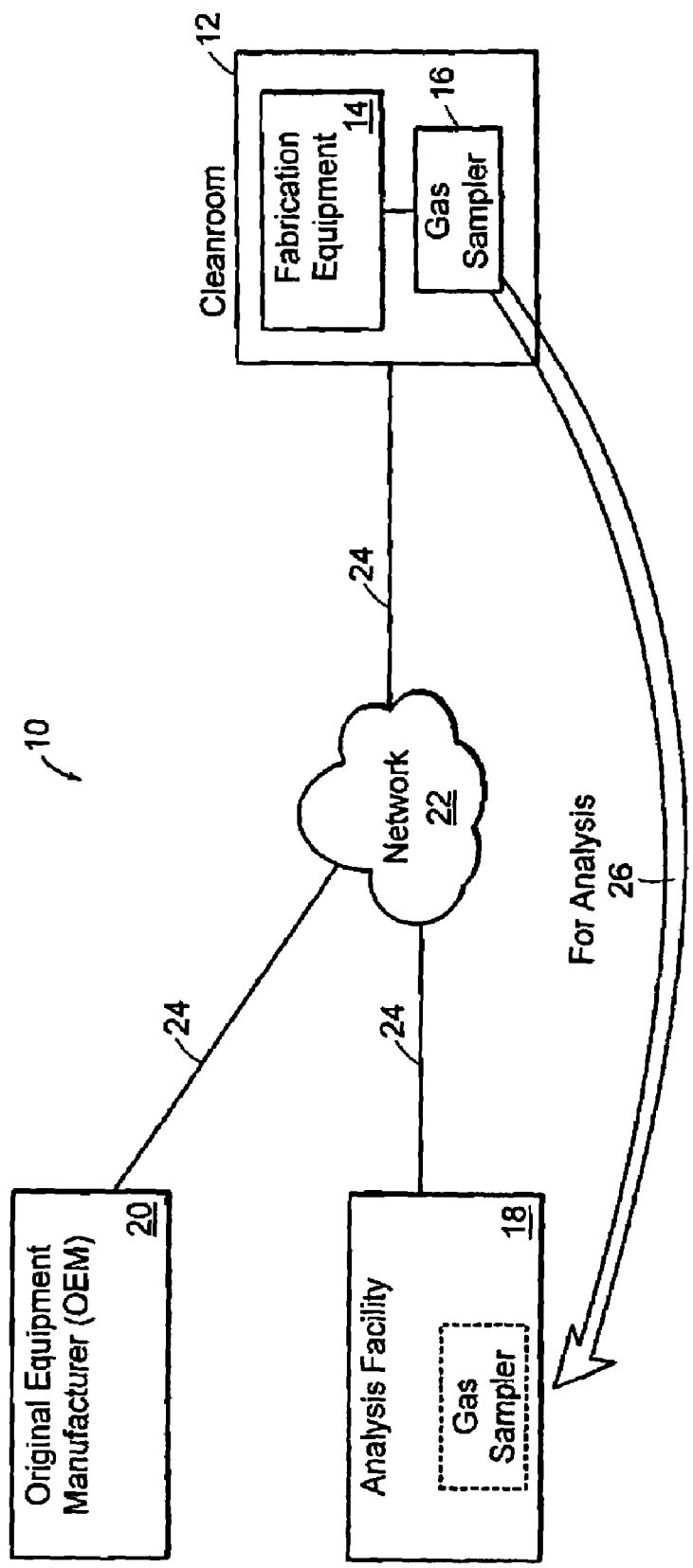
FIG. 1 illustrates a schematic representation of a system for collecting and analyzing contaminants consistent with embodiments and aspects of the invention.

FIG. 1 contains a schematic representation of a system for measuring and analyzing contaminants using a preferred embodiment of the invention, system 10 includes a cleanroom 12 having semiconductor fabrication equipment 14 operating therein, a gas sampling unit 16, a gas sampler analysis facility 18, an original equipment manufacturer (OEM) 20, a communications network 22, and communications links 24. Cleanroom 12 is used in the manufacture of semiconductor devices, such as silicon wafers. Within cleanroom 12, one or more pieces of fabrication equipment 14 are operating. Examples of fabrication equipment 14 are, but are not limited to, photolithography machines and chemical vapor deposition systems. Gas sampling unit 16 is placed in cleanroom 12 to sample contaminants present therein. Gas sampling unit 16 may be coupled to one or more pieces of fabrication equipment 14 using, for example, Teflon tubing, or gas sampling unit 16 may be located such that it draws ambient cleanroom air through the sampling devices located therein. Gas sampling unit 16 contains one or more internal sampling devices to sample contaminants present in cleanroom 12. For example, gas sampling unit 16 may contain sampling devices for measuring acids, bases and organic contaminants.

When gas sampling unit 16 is used, it samples a gas flow within cleanroom 12 for a determined period of time. When sampling is complete, inlet and outlet valves on gas sampling unit 16 are closed by the user, or alternatively may be closed automatically, to prevent additional gas from entering the unit. Then the user returns gas sampling unit 16 to analysis facility 18. For example, a user may return gas sampling unit 16 to analysis facility 18 using a common carrier 26 such as Federal Express™, United Parcel Service™ (UPS), or by way of a governmental postal service.

Upon receipt, analysis facility 18 opens gas sampling unit 16 and analyzes the quantity and/or type of contaminants present inside each sampling device. When finished, analysis facility 18 replaces the used sampling devices with new devices and re-seals the unit. Now reconditioned, the gas sampling unit 16 is returned to the user to facilitate additional sampling of cleanroom 12. Analysis facility 18 also provides sampling results to the user and/or OEM 20. Sampling results may be conveyed to an operator of cleanroom 12 by way of network 22 and communications links 24. OEM 20 may provide analysis facility 18 and cleanroom 12 with minimum contaminant levels as part of a cleanroom certification program. In such an instance, analysis facility 18 can inform cleanroom 12 as to whether it met the OEM criteria. In addition, analysis facility 18 may report the results directly to the OEM 20 so that it can maintain records pertaining to the certification of cleanroom 12 as suitable for the installation and operation of fabrication equipment 14.

Exemplary Method for Use

Figure 2:
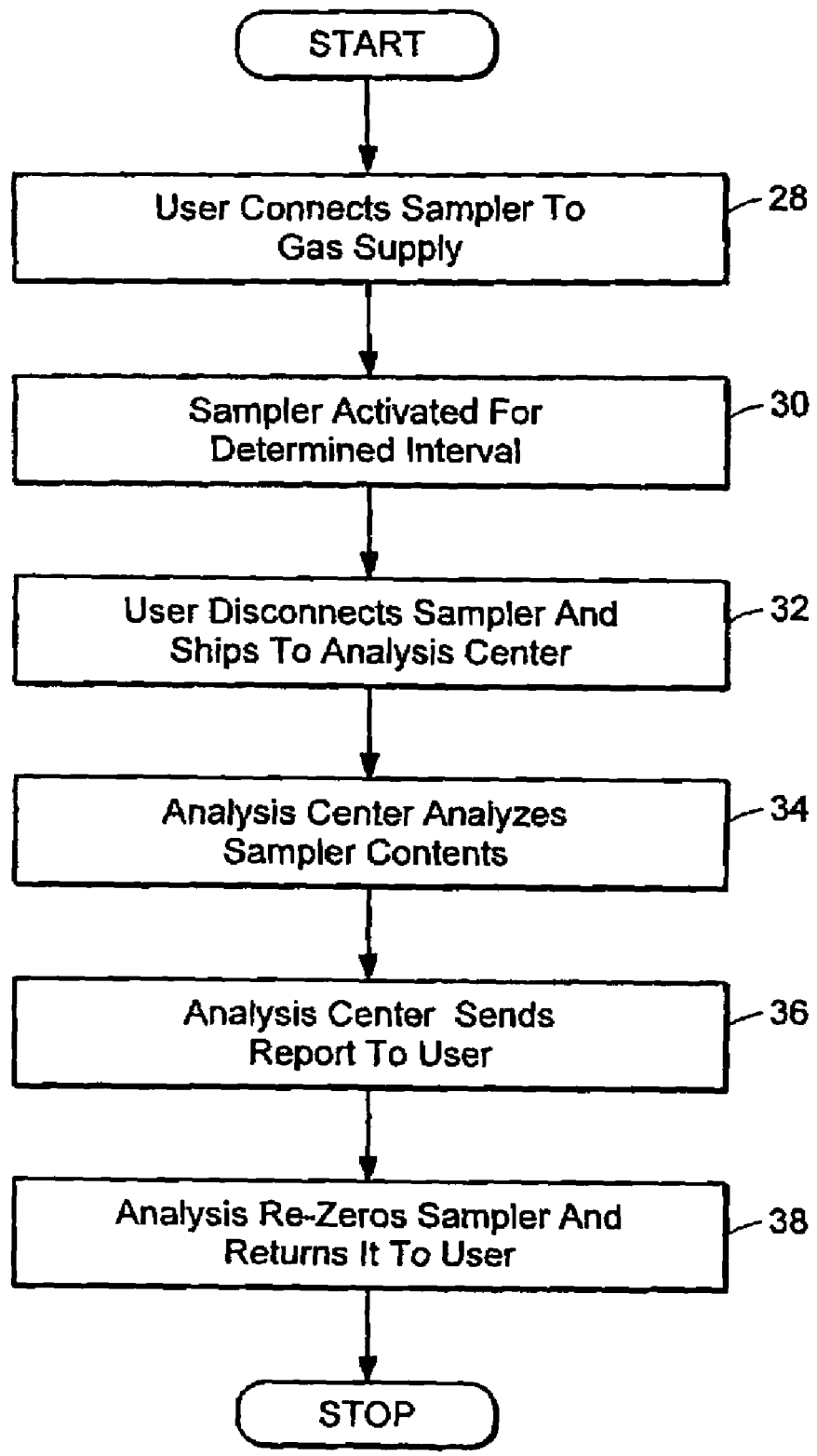
FIG. 2 contains a flow chart illustrating a method for using a dry sampler to measure contaminants.

FIG. 2 illustrates an exemplary method for employing gas sampling unit 16 to measure contaminants. A user, or operator of cleanroom or semiconductor processing system 12, connects gas sampling unit 16 to a gas supply within cleanroom 12 (per step 28). Gas sampling unit 16 is then activated for a determined time period (per step 30). When gas sampling unit 16 has operated for the desired time period, the user disconnects the unit and returns it to analysis facility 18 by common carrier (per step 32). The analysis facility 18 analyzes the contents of gas sampling unit 16 (per step 34) and sends the user, or customer, a report containing the results obtained from the unit (per step 36). In addition, the analysis facility 18 reconditions the gas sampling unit 16 so that it can be reused by the customer (per step 38). In order to recondition the gas sampling unit 16, some components within the unit may have to be replaced, while other components can be reset mechanically, chemically and/or electronically without requiring replacement.

Exemplary Embodiment of Gas Sampling Unit

Figure 3A:
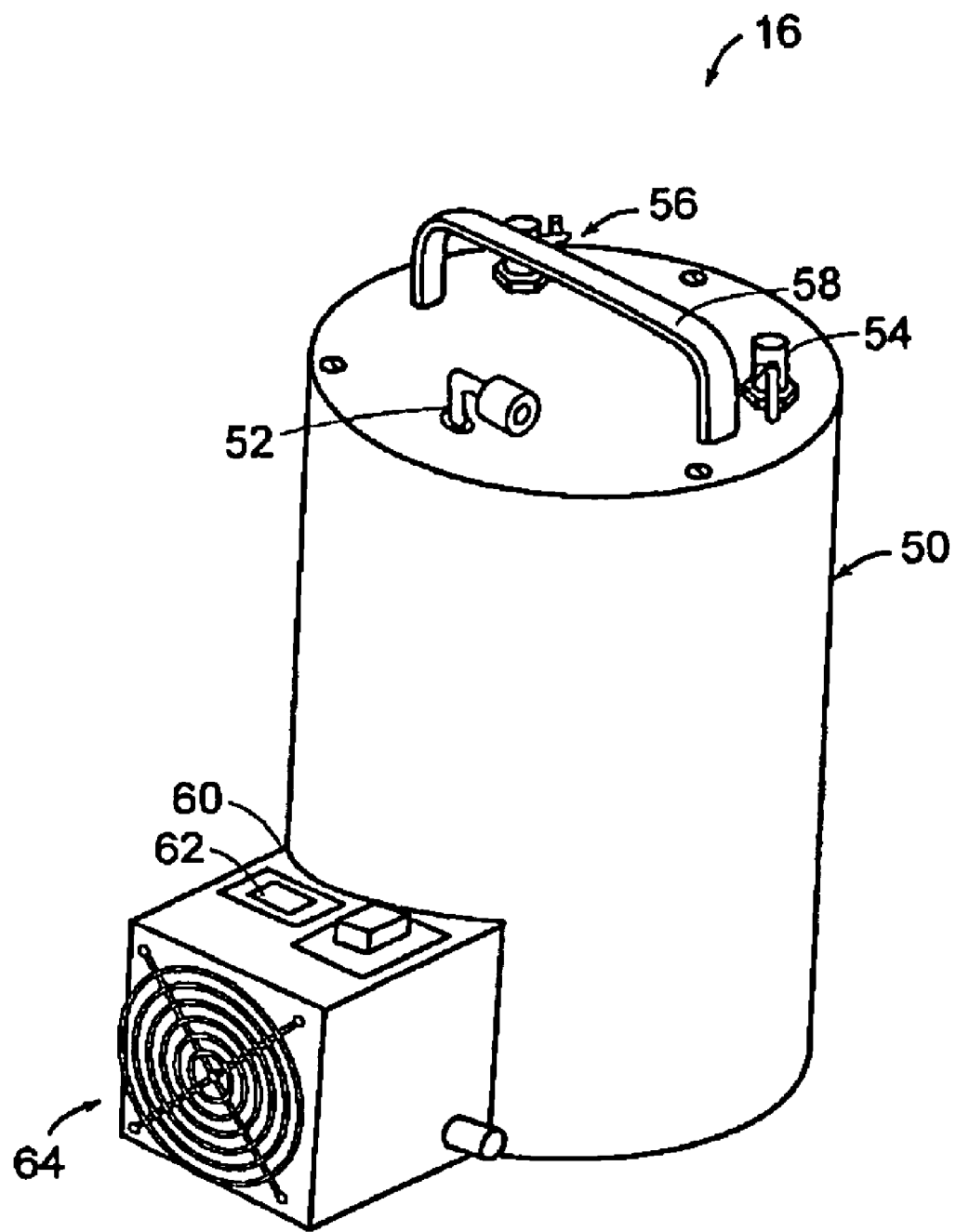
FIGS. 3A and 3B illustrate perspective views of the upper and side portion of a sampling system and or the lower portion of a sampling system, respectively.

FIG. 3A contains a perspective view of an embodiment of gas sampling unit 16. Embodiments of the invention are designed to be man-portable and typically weigh less than 20 lbs. The gas sampling unit 16 of FIG. 3A includes a housing 50, an inlet coupling 52, a first bypass/purge valve 54, a second bypass/purge valve 56, a handle 58, an ON/OFF switch 60, an hour meter 62 and a fan grating 64.

Housing 50 is adapted to sealably enclose internal parts and to protect them from incidental contact with foreign objects. In a preferred embodiment, housing 50 is made of aluminum; however, it can be made of, for example, plastic, composite, glass, and the like. In addition, housing 50 may be anodized or painted. Inlet coupling 52 is attached to a gas source and may consist of a NPT connector. First and second bypass/purge valves 54 and 56, respectively, are used to allow the input gas flow to bypass sampling components in order to ensure adequate gas flow is present without risking contamination of the sampling components within the gas sampling unit 16. Handle 58 provides a convenient and safe way for a person to transport gas sampling unit 16 without damage to the unit.

Embodiments of gas sampling unit 16 can be powered using external power sources such as alternating current (AC) obtained from a standard power receptacle or by way of internal power sources such as batteries. ON/OFF switch 60 is used to turn the unit on before sampling a gas flow in a cleanroom 12, and ON/OFF switch 60 is used to turn the unit off when sampling is complete. Hour meter or clock 62 is used to indicate how long gas sampling unit 16 has been run. Hour meter 62 may serve only as an indicator or it may be configured to automatically turn off gas sampling unit 16 when a predetermined operating interval has been reached. Fan grating 64 houses the blades of an internal cooling fan (shown in FIG. 5B).

Figure 3B:
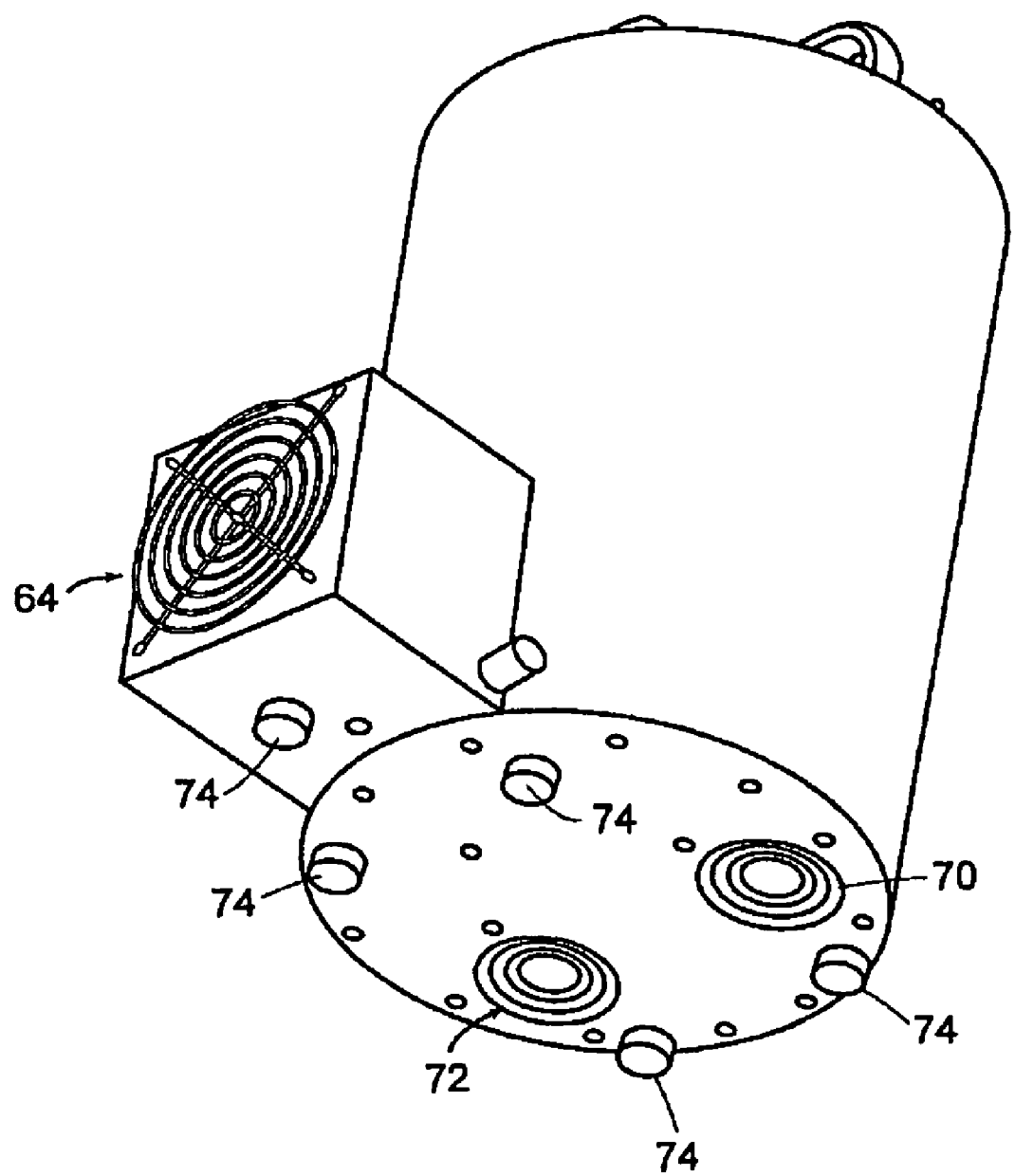

FIG. 3B contains a perspective view of the bottom of gas sampling unit 16 showing feet 74, a first outlet grate 70 and a second outlet grate 72. Gas sampling unit 16 may include a plurality of feet for causing the base of the unit to stand a determined distance above a surface upon which the unit is supported, such as a floor or bench top. Feet 74 may be made of compliant material such as rubber, silicone, Teflon, and the like. First outlet grate 70 and second outlet grate 72 are designed to protect the blades of the first and second exhaust fans, respectively. If desired, first outlet grate 70 and second outlet grate 72 may be positioned above ventilated sections of cleanroom flooring for exhausting into a cleanroom exhaust system. In other implementations, gas sampling unit 16 may exhaust into an ambient environment within a cleanroom 12.

Figure 3C:
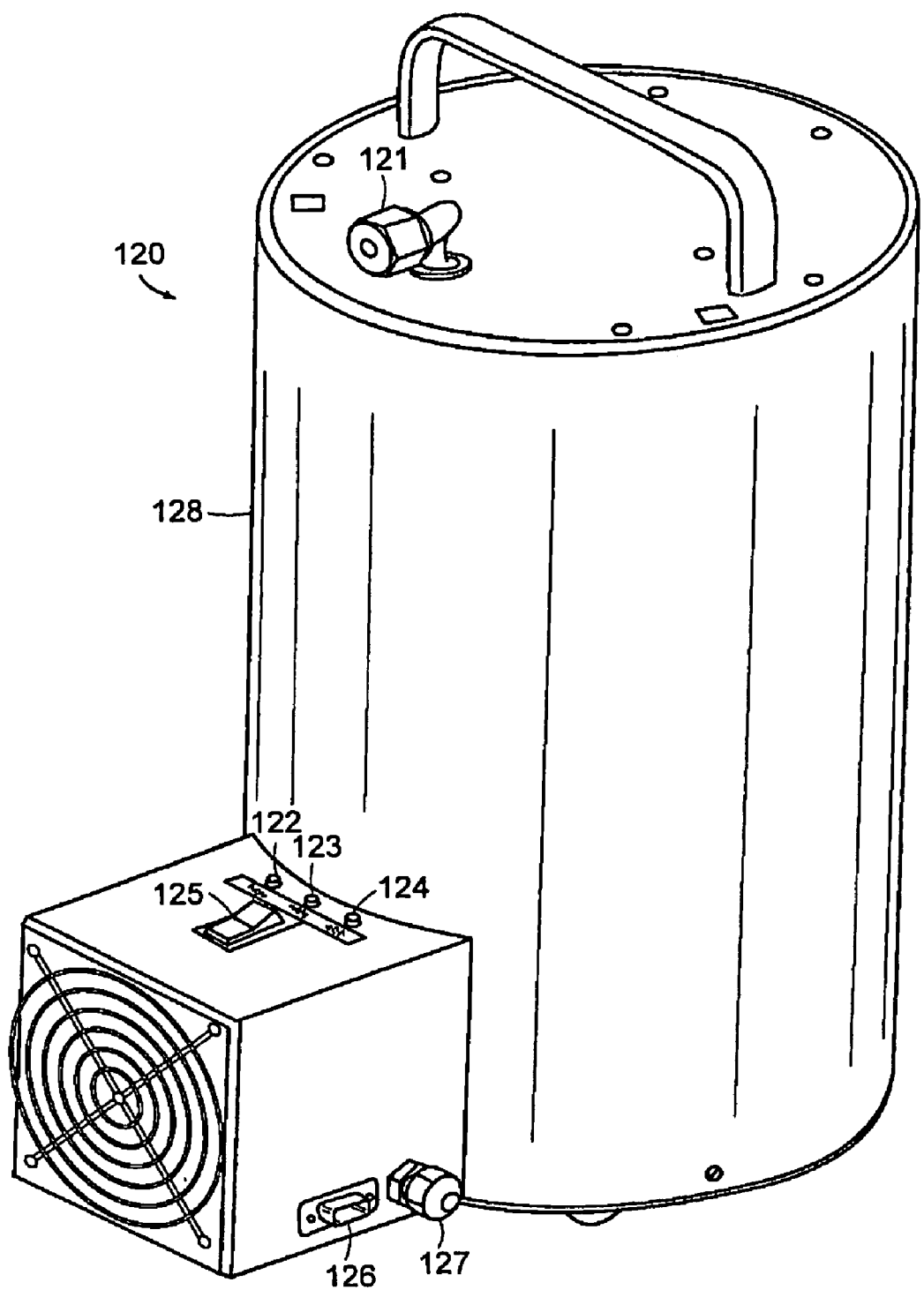
FIG. 3C illustrates another preferred embodiment of a sampling system in accordance with the invention using an automated value control system.

Illustrated in FIG. 3C is another preferred embodiment of the invention in which the manual valves 54 and 56 have been removed to provide a fully automated control system. In this automated sampling system 120, the inlet port 121 is positioned on the top of the housing 128. The start button or switch 125 provides the user with the one-step of starting an operative sequence with switch 125. The unit, 120 then automatically performs a sequence of electronically stored instructions. A first indicator 122, such as a yellow light (LED), can indicate that a purge of the system is being performed. A second indicator 123, such as a blue LED light, can be used to indicate that the system is performing a sampling operation. A third indicator 124, such as a green LED light, can indicate that the sampling operation is complete and the sampling elements, such as traps or impingers, can be removed for analysis. An interface (e.g. RS-232) connector 126 can be used to access the system controller and memory for programming system operation or to retrieve operational data stored in system electronic memory. Power cable 127 provides a power source to the system.

Figure 4:
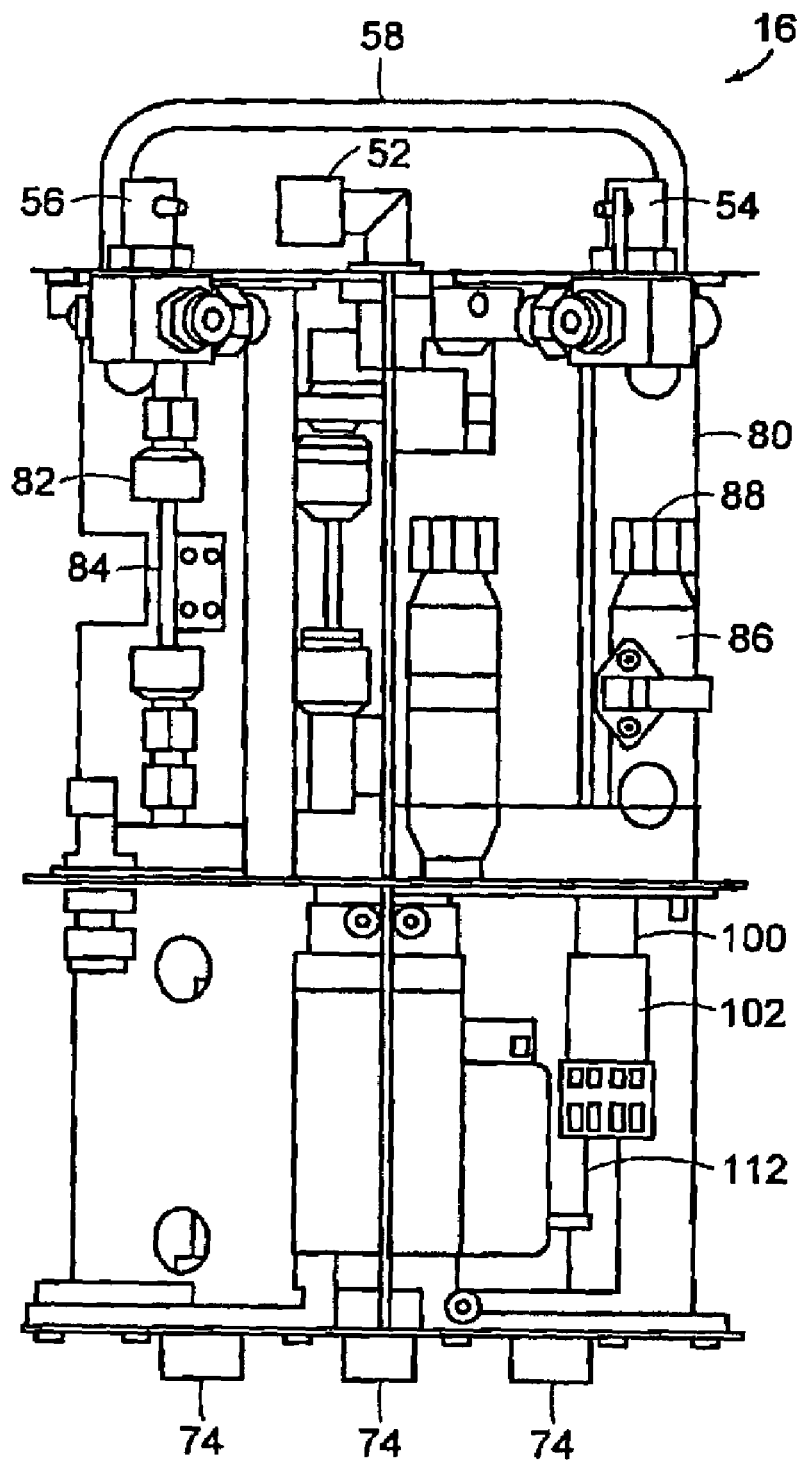
FIG. 4 illustrates a side view of a dry sampler in accordance with an embodiment of the invention.

FIG. 4 contains a side view of gas sampling unit 16 showing, among other things, entry manifold 80, a first dry trap 82 and a second dry trap 84 that both collect bases, such as ammonia, a first wet impinger 86 and a second wet impinger 88, exit manifold 100, pressure regulator 102 and vacuum pump 112. Embodiments of gas sampling unit 16 may contain only dry traps, only Tenax traps, or a combination of dry traps and Tenax traps. In addition, alternative embodiments of the invention may include one or more wet traps configured in series or in parallel along with the dry media sampling devices above. Employing wet sampling media alongside dry sampling media in gas sampling unit 16 makes possible a comparison of results obtained using wet media against results obtained using dry media. Such a comparison may be useful for calibrating new dry media sampling technologies against more readily known wet media sampling technologies.

Figure 5A:
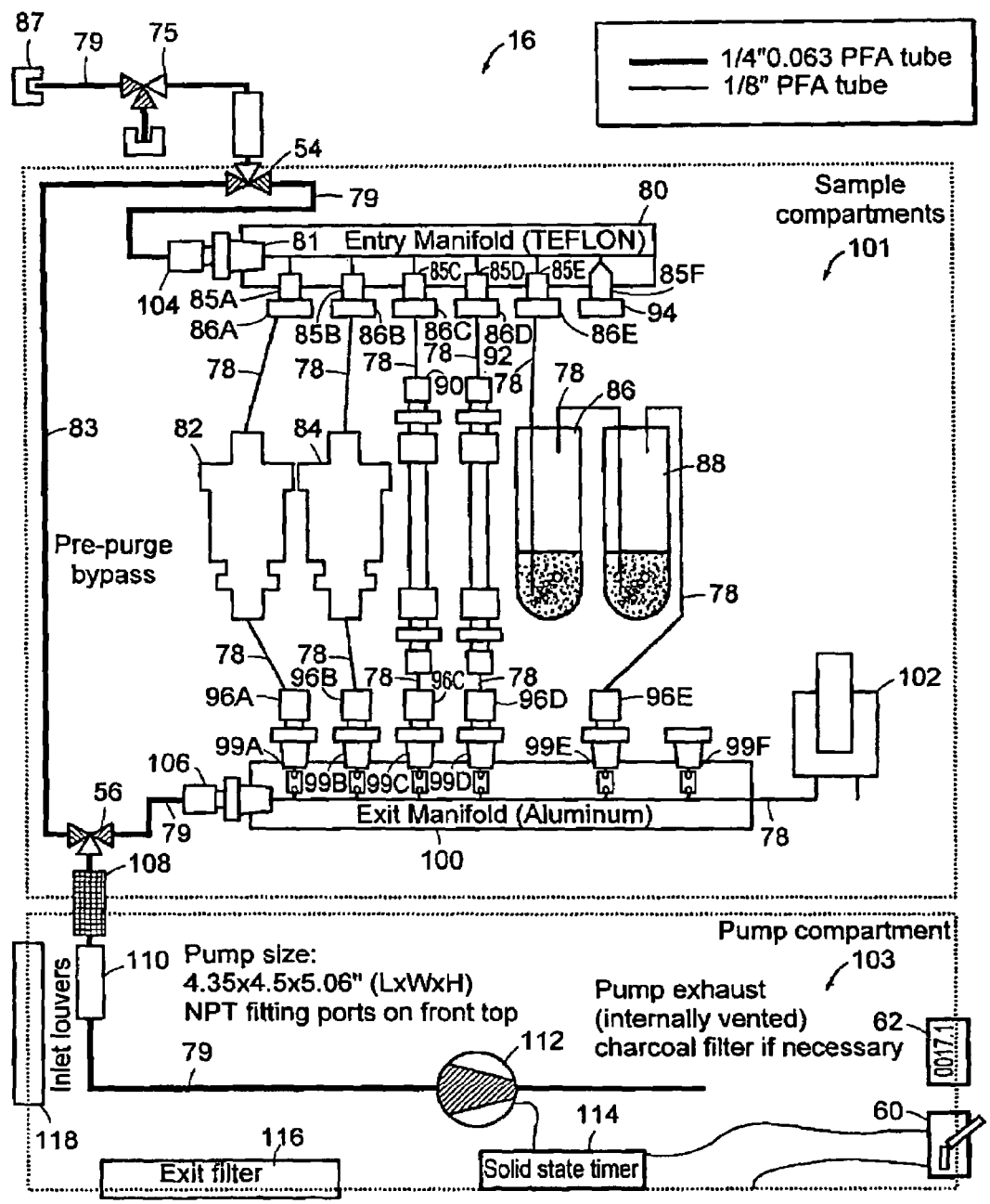
FIG. 5A illustrates a schematic representation of the gas sample processing path for a sampler system.

FIG. 5A contains a schematic diagram showing the components of FIG. 4 along with connections, fittings and additional components. A gas sample is received by way of sample inlet 87. Sample inlet 87 may be made of, for example, Perfluoroalkoxy (PFA) tubing having a diameter of approximately 0.25 inches. The gas sample then passes through PFA tubing 79 to tee connector 75 and then to the input of first bypass/purge valve 54. The first output of first bypass/purge valve 54 is coupled to a pre-purge bypass line 83 which runs to a first output of second bypass/purge valve 56. The pre-purge bypass line 83 is used to direct an incoming gas sample directly to exit manifold 100 while bypassing entry manifold 80. The second output of first bypass/purge valve 54 is coupled to an input port 81 of entry manifold 80 by way of tubing 79 and entry manifold connector 104. In a preferred embodiment, entry manifold connector 104 is a ⅛" NPT connector.

Figure 5B:
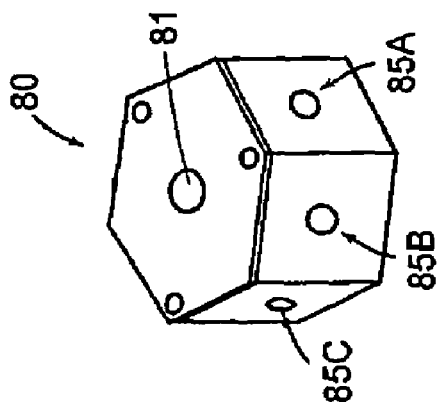
FIGS. 5B-5E illustrate a perspective view, a top view, a cut-away view and a side view, respectively, of an exemplary entry manifold in accordance with a preferred embodiment of the invention.
Figure 5D:
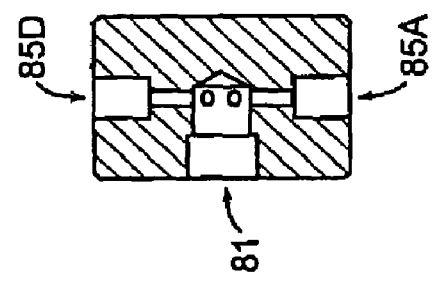
Figure 5C:
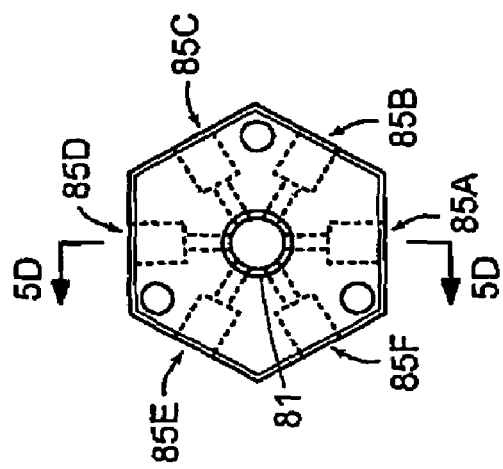
Figure 5E:
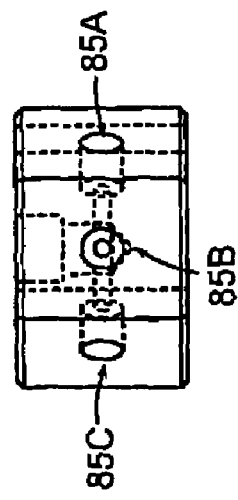

Entry manifold 80 is preferably machined from a material that will not outgas in the presence of anticipated contaminants contained in the gas sample. In a preferred embodiment, entry manifold is machined from analytical grade Teflon. Entry manifold 80 makes the gas sample available to sampling devices such as first dry trap 82, second dry trap 84, first Tenax trap 90, second Tenax trap 92, first wet impinger 86 and second wet impinger 88. Entry manifold 80 may also include a plug 94 for providing access to internal gas passageways disposed therein. Entry manifold 80 may be coupled to the sampling devices using manifold output connectors 86A-E, collectively 86, and sampling device tubing 78. Sampling device tubing 78 may consist of PFA tubing having a diameter on the order of ⅛". FIG. 5B illustrates a perspective view of an embodiment of entry manifold 80 having a width of approximately 1.5 inches and a height of substantially 1.0 inches. Entry manifold 80 has input port 81 and a plurality of output ports 85A-85F. FIGS. 5C-5E illustrate a top view, a cut away view and a side view of entry manifold 80, respectively. The sampling devices, such as the traps and impingers referenced above, are further discussed in further detail in conjunction with FIGS. 6-14.

Figure 5F:
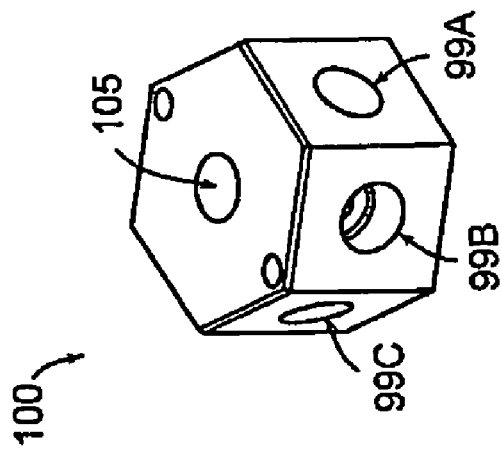
FIGS. 5F-5H illustrate a perspective view, a top view and a side view, respectively, of an exemplary exit manifold in accordance with a preferred embodiment of the invention.
Figure 5H:
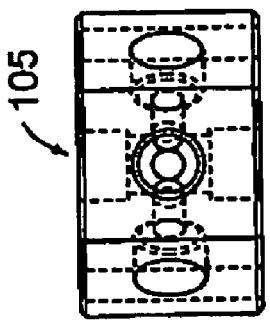
Figure 5G:
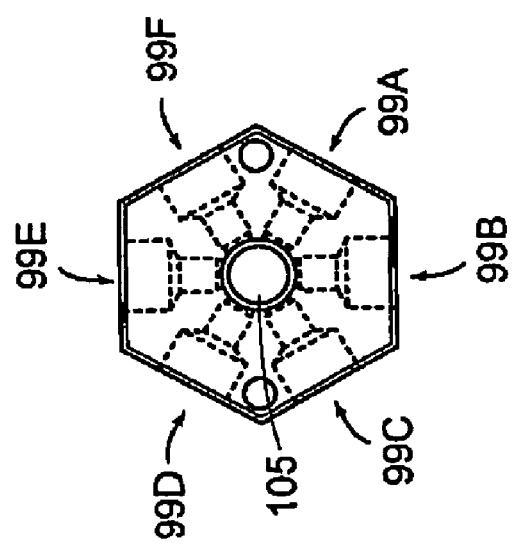

The outputs of the sampling devices are coupled to exit manifold 100 by way of sampling device tubing 78 and exit manifold connectors 96A-E, collectively 96. In a preferred embodiment, exit manifold connectors 96 of ⅛" tube to ⅛" NPT male connectors and are made of Nylon. Exit manifold 100 can be made from a metal, such as aluminum, and can be equipped with threads for allowing exit manifold connectors 96 to be threadably inserted thereto. Exit manifold 100 may further have a ⅛" NPT plug. FIG. 5F illustrates a perspective view of exit manifold 100. Exit manifold 100 includes a plurality of input ports 99A-99F and an exit port 105. FIGS. 5G and 5H illustrate alternative views of exit manifold 100. Exit manifold 100 is still further coupled to the second output of second bypass/purge valve 56 by way of tubing 79 and exit manifold bypass connector 106.

Note that another preferred embodiment replaces one or both manifolds with a set of fittings and valves to control fluid flow.

A pressure regulator 102 is employed to ensure that a constant pressure is present in exit manifold 100 during operation of the gas sampling unit 16. The pressure regulator 102 may be a passive device or may be active. An active pressure regulator employs electrical signals for making measurements and for controlling the operation of the regulator.

The sampling components, tubing, couplers and connectors may be grouped and located proximate to each other in a sample compartment 101 within gas sampling unit 16. For example, in the embodiment illustrated in FIG. 3A, sample compartment 101 is located in the upper portion of the unit 16, while the pump compartment 103 is located in the lower portion of the unit 16.

A vacuum pump 112 is used to draw a gas sample through the pre-purge bypass line or through entry manifold 80, the sampling components (collectively 82, 84, 86, 88, 90, 92) and exit manifold 100. Vacuum pump 112 is electrically powered by way of batteries or conventional AC power obtained from a standard wall outlet. NPT fittings may be employed for coupling tubing 79 to the input of vacuum pump 112 and for directing the exhaust from the output of vacuum pump 112. In a preferred embodiment, vacuum pump 112 operating in conjunction with pressure regulator 102 maintains a pressure of twenty inches of mercury. A charcoal back diffusion trap 108 and check valve 110 may be employed to ensure that vacuum pump 112 cannot inject a gas sample into the sampling components by way of backflow. A solid state timer 114 may be used to control operation of vacuum pump 112. Gas sampling unit 16 may be powered by way of standard AC voltage (typically 110 v or 220 v). Furthermore, a combination fuse and ON/OFF switch 60 may be used to turn the unit on and off. In addition, gas sampling unit 16 may include an hour meter 62 for tracking sample times and total usage of the unit. Gas sampling unit 16 may further include inlet louvers 118 for allowing cooling air into the unit and gas sampling unit 16 may include an exit filter 116 for removing airborne contaminants before exhaust air is released to the exterior of the unit.

Figure 5I:
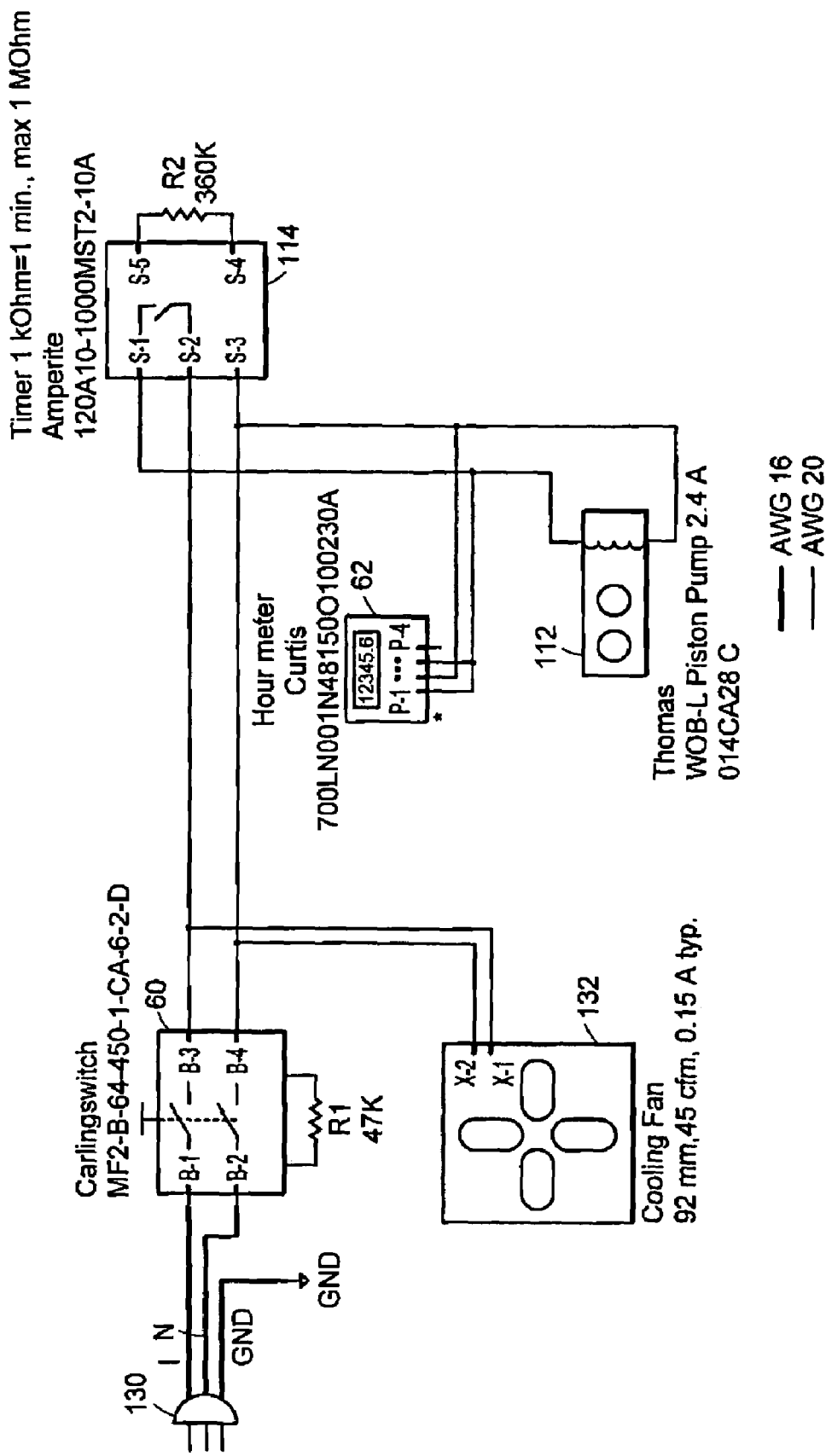
FIG. 5I illustrates a schematic representation of electrical components associated with a preferred embodiment of the invention.

FIG. 5I illustrates a schematic diagram showing electrical components used with gas sampling unit 16. A wall plug 130 is electrically coupled to a power source so that power is supplied to ON/OFF switch 60. ON/OFF switch 60 couples the power, with and/or without attenuation, to solid state timer 114, hour meter 62, vacuum pump 112 and cooling fan 132.

Exemplary Dry Trap

A dry sampler of the present invention can be used in several system configurations including "active sampling" and "passive sampling". As used herein, "active sampling" refers to the use of air moving device which utilizes an external source of energy coupled to the sampling system to deliver a gas sample to a collection material of a dry sampler of the sampling system. In comparison, passive sampling uses the energy of the gas sample itself to deliver a gas sample to a collection material of a dry sampler, for example, by diffusion. A dry sampler can also be used in sampler system configurations such as those found in co-pending U.S. application Ser. No. 10/395,834, the entire contents of which is herein incorporated herein by reference.

Figure 6A:
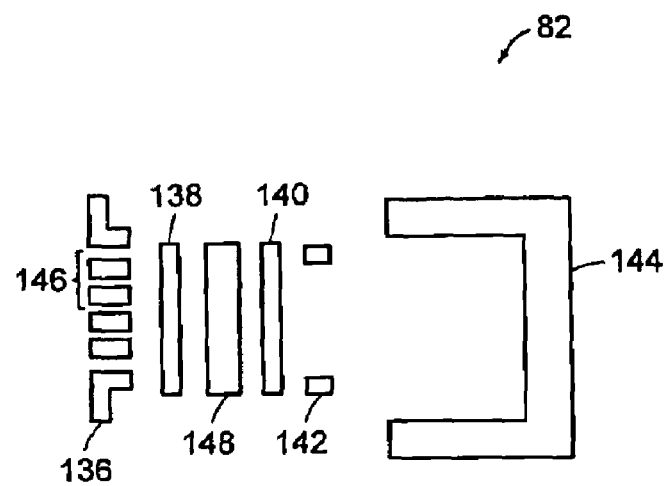
FIGS. 6A and 6B illustrate exploded cross-sectional views of various embodiments of a dry sampler in accordance with the present invention.

FIG. 6A illustrates an exemplary embodiment of first and second dry traps 82 and 84, respectively. Dry trap 82, 84 includes a perforated end cap 136, one or more screens 138, one or more collection pads or media element 148 for sampling, a support structure 140, and a retaining ring 142 (such as, for example, an O-ring) in a sampler body 144. The end cap includes several channels 146 to allow passage of an air sample to the collection 148. This embodiment is an example of a passive sampler in which contaminants are collected in a collection media by diffusion.

Figure 6B:
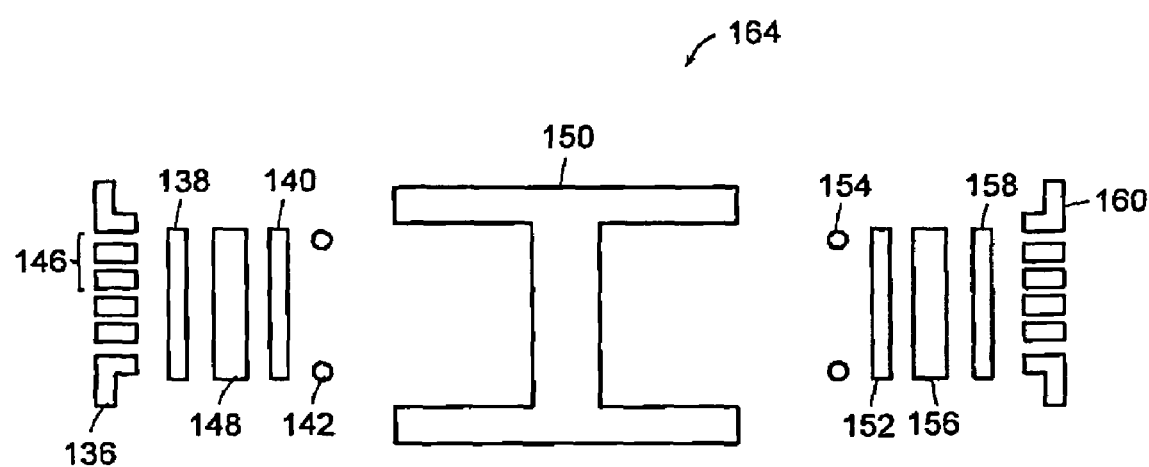

FIG. 6B depicts a dual passive dry sampler configuration that includes a second separate stack 164 of end cap 160, one or more screens 158, one or more collection pads 156, a support structure 152, and retaining ring 154 in the sampler body 150. In various embodiments, for example, one stack of a dual dry sampler configuration is used to sample a volume or air stream of interest while the other stack is used to sample ambient conditions.

Preferably, the perforations in the end cap and opening in the one or more screens are chosen to ensure the intake rate of the species of interest is diffusion limited. In various embodiments, an end cap or end cap and screen combination can be used to provide variable restriction of air flow into the sample. For example, in one embodiment, the intake rate for ammonia is about 16.7 cm³/min. utilizing an end cap with a total opening cross-sectional area of about 0.785 cm² composed of channels about 0.6 cm long and one stainless steel mesh screen with a total opening cross-sectional area of about 0.152 cm² composed of channels about 0.02 cm long. As is understood by those of skill in the art, intake rate varies with diffusion constant. The mass uptake can be estimated from Fick's law using the equation, $$Q = \frac{DACt}{L},$$

(1) where Q is the mass uptake, D the diffusion coefficient, C the gas concentration, t sampling time, A the cross sectional area of the diffusion channel, and L is the length of the diffusion channel.

The collection pad comprises a collection material, which is preferably a treated fibrous media. For example, for ammonia sampling, acid treated quartz fibrous media is preferred. A wide variety of acids, of suitable pKa, can be used for ammonia sampling including, but not limited to, citric acid. Preferred acids include those which have a low ammonia background (such backgrounds can arise, for example, from reactions within the sampler and/or upon subsequent treatment and analysis). Collection materials include, but are not limited to those listed in Table 1, which include ion exchange resins, zeolite, silica gel, and treated Tenax-TA®, in addition to treated fibrous media.

Prior art dry traps employ binders, such as for example glycerin, as coatings on the loosely woven fibrous media used therein. These prior art devices use binders to facilitate retention of acids contained within a sampled gas supply. In contrast, preferred embodiments use a more tightly woven fibrous media without binders. Employing binders in connection with preferred embodiments actually reduces the ability of the fibrous media to retain gas borne acids because the binders coat granules disposed along the fibers rendering them less available to contaminants.

(see, for example, M. Niwa, N. Kanada, M. Sawa et al "Temperature-programmed desorption of ammonia with readsorption based on the derived theoretical equation" J. Phys. Chem 1995, 99, p. 8812-8816; and T. Masuda, Y. Fujikata, H. Ikeda et al "A method for calculating the activation energy distribution for desorption of ammonia using TPD spectrum obtained under desorption control conditions" Applied Catalysis A:General 162 (1997), p. 29-40); the entire contents of both these publications are hereby incorporated by reference). However, the TPD method contains a complex behavior relating to the readsorption and diffusion in the zeolite framework.

Silica gel, an amorphous form of silica, is another example of a collection material where electrically polar active sites on the surface provide a high affinity to polar molecules like ammonia. Polar adsorbents can be used for short duration sampling of gaseous challenges at relatively low humidity, so that the adsorbent does not become saturated with water vapor before sampling is complete. Among important advantages of silica gel is: desorption of contaminants can be easily accomplished with a variety of solvents such as alcohols and water and can be even automated through application of solid phase extraction (SPE) devices available on the market place (Perkin Elmer, Dynaterm and others). Application of other non-porous, fibrous systems followed by SPE is also feasible.

The results shown in Table 1 were obtained from collection materials handled as follows. For the zeolite data of Table 1, zeolite 13X, (sodium form, pellets) was received from Kurt J. Lesker Inc. and then ground and sieved to obtain ³⁄₄₀ fraction. The sample of zeolite was pre-treated at 600° C. in a quartz boat with a flow of filtered clean dry air (CDA) overnight and then loaded into ½" quartz tube (1.5-2 gr) with quartz wool to support the adsorption bed. An ammonia capacity test was conducted with a known ammonia challenge (with CDA and humidified CDA as make-up gas) and total molecular base real time monitor showed about 600 L/gr breakthrough volume (minimum sample volume collected should be about 240 L to reach LDL of 0.1 ppbV by IC). A limited series of TPD tests which immediately followed after loading the adsorp-

TABLE 1

Tested "dry" collection materials

| Feature | Ion exchange resin | Zeolite-13x | Silica gel | Acid treated Tenax-TA | Acid treated quartz fibrous media |
|---|---|---|---|---|---|
| Presence of liquid phase | No | No | No | No | No |
| Initial background | Medium | Medium | Low-High | Medium | Low |
| Capturing efficiency | Yes | Yes | Yes | Yes | Yes |
| Detection limit | >0.1 ppb | >0.1 ppb | >0.1 ppb | >0.1 ppb | 0.1 ppb |
| Flow (portable Pump, 1 lpm) | Yes | Yes | Yes | Yes | Yes (up to 3 lpm tested) |
| Bacterial degradation | Not tested | Not tested | Not tested | Not tested | Not tested |
| Sample recovery efficiency | ~50-70% (multiple extractions) | ~50% (multiple desorptions) | 50-60% (extraction) | Inconclusive results | close to 100% |
| Storage efficiency | Not tested | Failed | Not tested | Not tested | Passed lab tests |
| Analytical procedure | DI extraction + IC | Thermodesorption + IC | DI extraction + IC | Thermodesorption + IC | DI extraction + IC |
| Reusable | No | Yes | No | Yes | No |
| Simplicity | No | No | No | No | Yes |
| Cost | Medium | High | Medium | High | Low |

In various embodiments, zeolites can be used as a collection material, specifically zeolites with mild "acidity" can be used for ammonia "scrubbing". Temperature-programmed desorption (TPD) is a relatively simple and reproducible method for ammonia recovery in studies of zeolites acidity tion bed with a known amount of ammonia (VICI calibrator with permeation device, loaded about 0.3 μg of ammonia and He as the desorption gas was used to avoid secondary reactions of ammonia at high temperature on zeolite, 500° C.—desorption temperature) showed about 50% recovery of ammonia in a series of 2-3 desorption cycles. In a series of "storage efficiency" tests when "pre-baked" zeolite bed was loaded with ammonia (about 0.3 μg) and then stored in the capped tube overnight, TPD elevated levels of ammonia-as high as about 4-6 μg were measured, indicating that the source of the contamination apparently is in the zeolite. Repetitive tests consistently showed elevated levels of ammonia.

For the silica gel data of Table 1, silica gel was used in the form of packed so-called ORBO™-507 tubes (Supelco). Ammonia capacity tests showed satisfactory results. The tubes had greater than 300 L/per tube "breakthrough volume" at a flow of 1 Lpm and challenge level about 20 ppb of ammonia. The "breakthrough volume" is defined as the total gas volume delivered through the tube at which trap collection efficiency drops below 100% for a particular contaminant of interest. Measurements of the ammonia background (extraction with DI water) of each part of unexposed tubes showed elevated and inconsistent ammonia levels between lots, which ranged from about 0.8 ppb to about 2.3 ppb (when derived from 240 L sample size and 10 cc of DI water for extraction). Measurements of extraction efficiency of ORBO-tube pre-loaded with ammonia (test similar to the above) showed about 50% efficiency in single extraction cycle.

Other non-porous media, for example, citric acid treated quartz fibrous media (Whatman) was deployed for ammonia "scrubbing" followed by DI water extraction and gradient IC analysis. Gradient elution was used for better separation of ammonia from sodium (see, for example, FIG. 11). The VICI calibrator, fitted with an ammonia permeation device, controlled ammonia gaseous challenges (known concentrations of ammonia) and clean room ambient air with 30-35% relative humidity (RH) were used for ammonia exposure.

Figure 7:
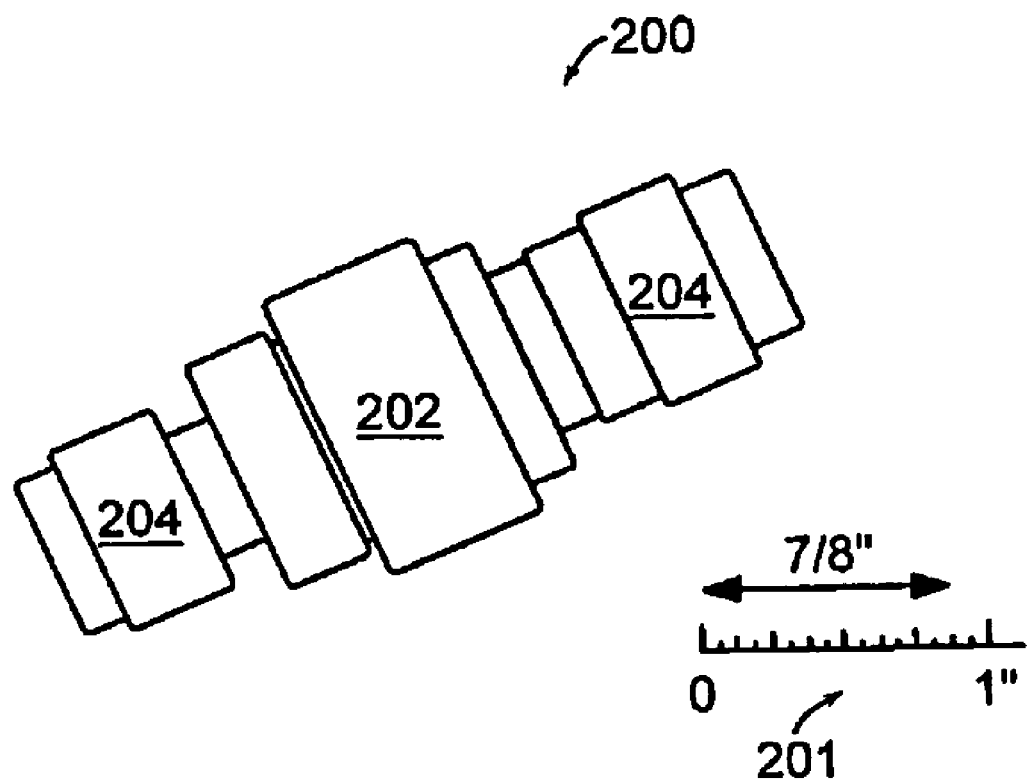
FIG. 7 is a photograph of an embodiment of an active dry sampler system configuration in accordance with the present invention.

For example, FIG. 7 is a drawing of one embodiment of a dry sampler of the present invention used in an active sampling configuration 200, where a ⅞" scale 201 is provided for reference. The collection pads are contained in the body 202 of a ½ inch nylon Swagelock™ type fitting. In use, one of the ends of the fitting 204 is connected to the volume to be sampled and the other end to an air moving device. In an active sampling system configuration, any support structure that may be used is chosen based on an acceptable pressure drop for the sampling system.

Figure 8:
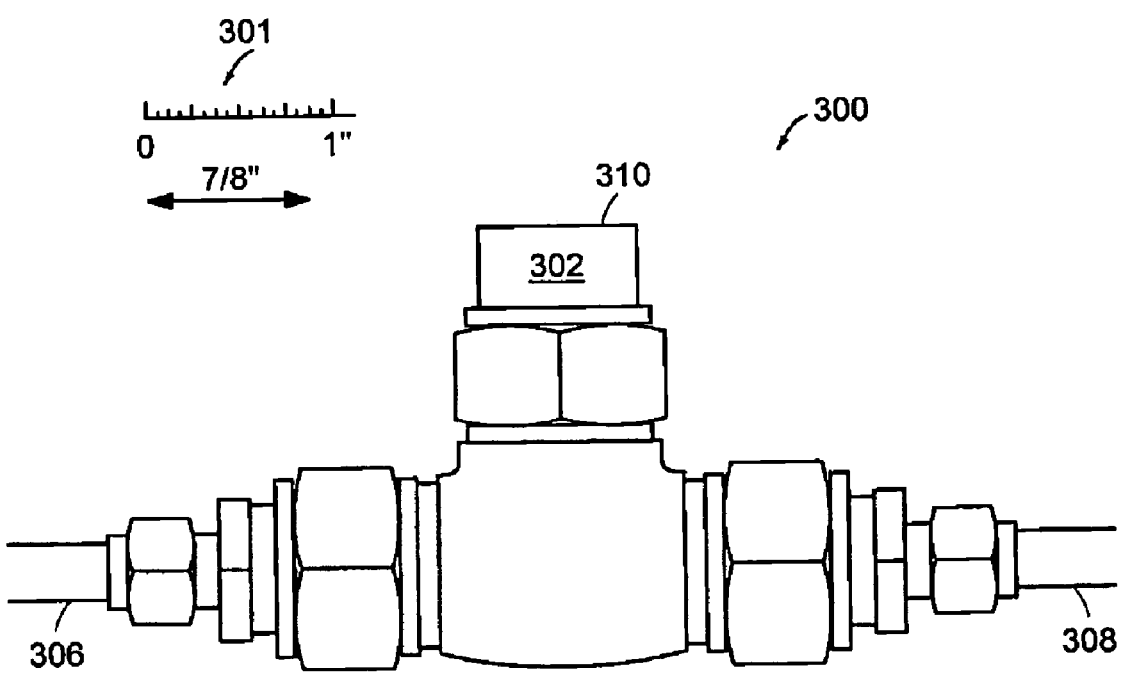
FIG. 8 is a photograph of another embodiment of a dry sampler system configuration in accordance with the present invention.

FIG. 8 is a drawing of one embodiment of a dry sampler of the present invention used in a passive sampling configuration 300, where a ⅞" scale 301 is provided for reference. The dry sampler 302 is placed in one arm of a Swagelock™ type T-union, a line 306 to the volume to be sampled is connected to another arm, and the last arm 308 is plugged. The dry sampler 302 depicted in FIG. 8 is a dual-type dry sampler where the upper dry sampler 310 is arranged to sample ambient air whereas the lower dry sampler (not visible within the T-union) samples gas provided by the sample line 306.

Figure 9:
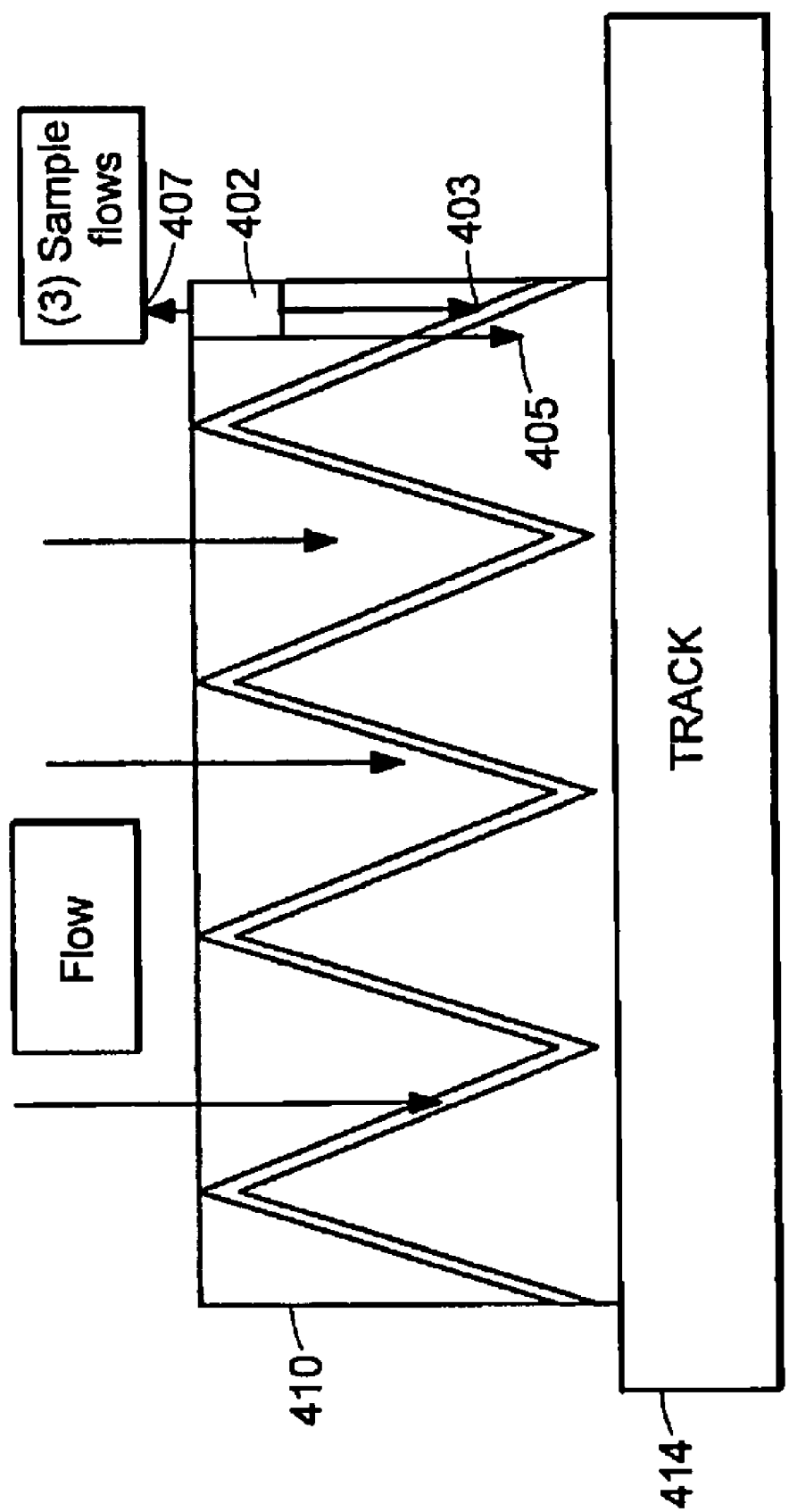
FIG. 9 illustrates a schematic view of an embodiment for monitoring an air stream using a sampler for a filter installed on a semiconductor tool, namely, a coat/develop track in accordance with the present invention.

In other embodiments, a dry sampler is located directly in contact with the air stream or volume to be sampled (thereby, for example, avoiding sample line contamination); using either passive diffusion or an active flow to collect the sample. For example, FIG. 9 schematically depicts the use of one or more dry samplers 402 to sample the air at various locations (upstream 403, inter-stack or inter-filter 405, and downstream 407) relative to a filter (or filter stack) 410 for the track 414 of a semiconductor processing system. Similar arrangements can be used to sample air in or being delivered to, for example, a filter cabinet or a semiconductor processing tool.

For example, the dry samplers of the present invention can be used to receive samples from ambient, between filter layers, and discharge and can be located within the filter body to avoid, for example, mechanical integration problems (e.g., obstructing the adjacent installed track filter). Dry samplers are preferably shipped sealed and are preferably automatically unsealed during installation (e.g., by removal of a cover screen or some other mechanism representative of installation unseals the sampler). In various embodiments, the installation process activates an electronic timer of the dry sampler system, which will start upon installation and trigger a visual and/or auditory alarm when a pre-set time (e.g., thirty days) is reached, and/or send a signal through a network connection to trip an alarm with either the track software or the fabrication facility manufacturing software control system, and/or send an email to the person who needs to know.

Preferably, the dry samplers of the present invention are allowed to sample a volume or air stream for a time sufficient to detect the molecule of interest at the detection level desired. The time sufficient to detect the molecule of interest at the detection level desired depends on the intake rate of a gas sample to collection material of the dry sampler. For example, where the molecule of interest is ammonia and the intake rate is about 16.7 $cm^3$/min., an intake volume of about 240 L (corresponding to an intake time of about four hours for active sampling at a flow rate of about 1 lpm) is preferred to achieve a LDL of 0.1 ppbV, whereas an intake volume of about 1200 L is preferred to achieve a LDL of 0.02 ppbV.

Figure 10:
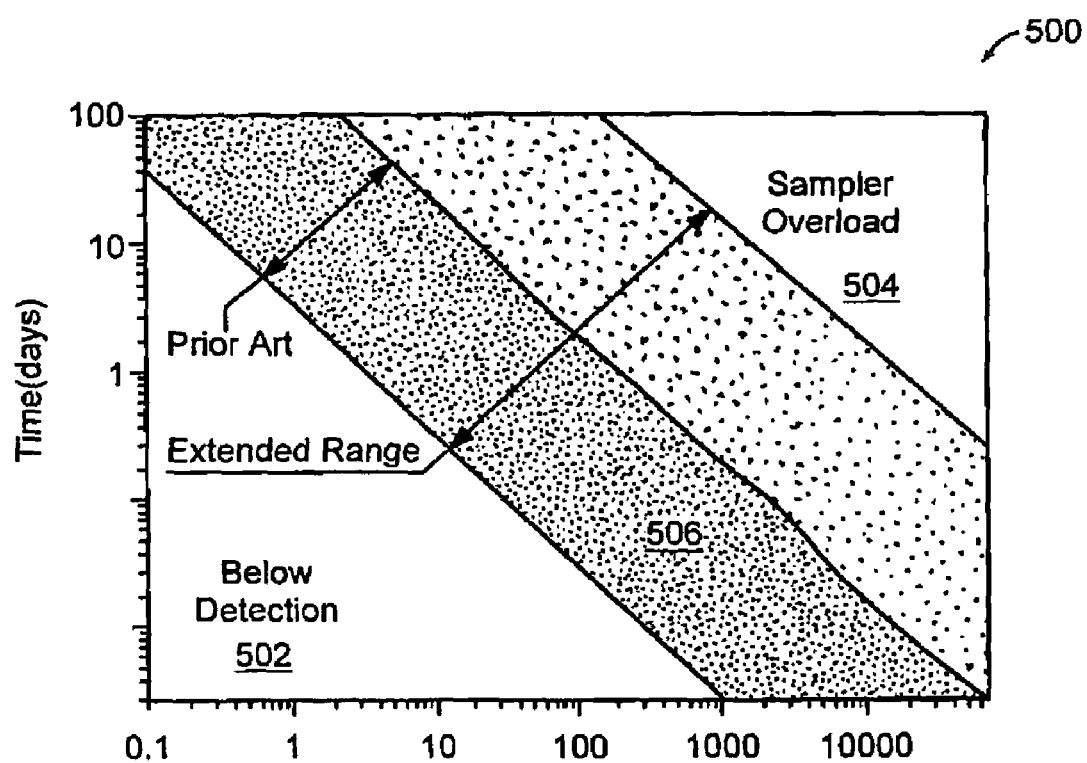
FIG. 10 is a graph for determining approximate sampling times for ammonia when using embodiments of dry samplers employing a passive sampling configuration in accordance with the present invention.

FIG. 10 is a log-log plot 500 for determining approximate sampling times for ammonia for various embodiments of dry samplers employing a passive sampling configuration in accordance with various embodiments of the present invention. The plot 500 assumes a collection material treated with about 1.5 milligrams of citric acid (or its weight equivalent) and an intake rate of 16.7 $cm^3$/min. to the collection material. The plot 500 gives an approximate value for the sampling time (x-axis in units of days) to reach a selected LDL (y-axis in units of $\square g/m^3$). The plot 500 illustrates three general regions, a region where the sampling time is insufficient to reach the LDL 502, a region where the collection material is overloaded 504 and a region where the LDL is reached but the collection material is not overloaded 506. It is to be realized, however, that the lower bound of the overload region 504 depended on the amount of collection material used, where an increase in the amount of collection material used increases the sampling time that can be used before overload.

Figure 11:
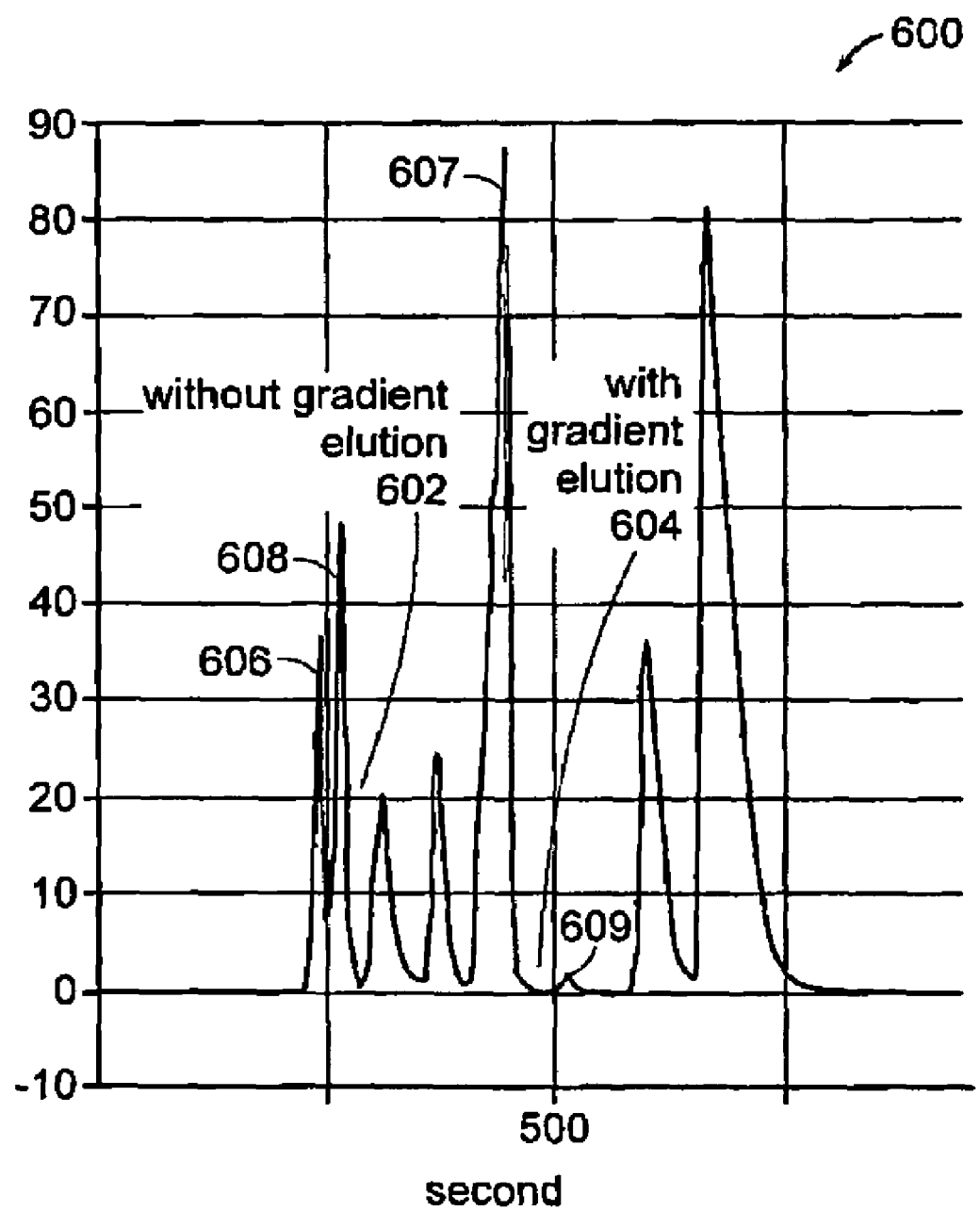
FIG. 11 illustrates ion chromatography elution profiles for a dry sampler in accordance with the present invention.

A wide variety of techniques can be used to analyze the collection material for the amount of the molecule of interest collected. In various embodiments, the molecule of interest, for example ammonia, is desorbed (for example, by thermal desorption) or extracted (for example, using DI water) from the collection material for analysis. Preferred method of analysis include, but are not limited to, gas phase chromatography mass spectrometry (GCMS) for molecules of interest desorbed into the gas phase, chemiluminescence (for example, for ammonia, by catalytic conversion of ammonia into NO, followed by chemiluminescent detection of the generated NO), fluorometry (for example, by addition of a suitable dye to the molecules of interest), and ion chromatography (IC) for molecules of interest extracted into a liquid phase. For example, FIG. 11 depicts examples of various elution profiles 600 of a collection material where the molecule of interest, ammonia, was extracted with DI water and IC was used to determine the amount of ammonia collected, and thereby the average concentration of ammonia in the volume of air sampled. Illustrated in FIG. 11 are set of profiles obtained without gradient elution 602, and a set obtained with gradient elution 604, where the first peak in each set 606, 607, corresponds to sodium (Na) and the second peak 608, 609 corresponds to ammonia.

FIG. 7 and FIG. 8 show general views of dry samplers deployed in these studies, some results of which are shown in FIGS. 12A-12D and Tables 4-10. The active dry sampling (ADS) used a citric acid treated quartz fibrous media pad and was connected to an external hand-held pump. The passive dry sampling configuration was placed into a stainless tee and was exposed to ammonia the same way as ADS but without an external pump (see, for example, FIG. 8). The uptake rate of ammonia, 16.7 $cm^3$/min was calculated based on the geometry of the flow restrictor (end cap) and, the diffusion coefficient of ammonia (W. J. Massman "A review of the molecular diffusivities of H2O, CO2, CH4, CO, O3, SO2, NH3 in air and nitrogen" Atmospheric Environment, 32(1998), p. 1111-1127.). Comparative studies were conducted in an attempt to find quartz fibrous media with minimal ammonia background as well as citric acid. Measurements were carried out to establish the initial ammonia background after treatment with citric acid and "storage efficiency" of acid treated pads in common nalgene bottles in the lab environment, some results of which are shown in Table 2. The data indicated that citric acid pre-treated quartz fibrous media pads have low ammonia background comparable with the DI water used for extraction, and they also may be stored at room temperature without significant deterioration over the time period studied. Similar results were obtained by placing freshly prepared acid treated quartz fibrous media pads into a nylon housing (for example, FIG. 7) and storing the assembly in the lab environment followed by extraction with DI, some results of which are shown in Table 3.

FIGS. 12A-12D and Tables 4-10 present the results of several comparisons ammonia concentration measurements obtained using traditional DI water wet impingers to those obtained using various embodiments of dry sampler and dry sampler system configurations of the present invention. As can be seen from the slope of the plot of ammonia concentration determined by a wet impinger technique versus that obtained using a dry sampler technique of the present invention, a high degree of proportionality is observed. In FIGS. 12A-12D the filled symbols represent values based on actual measurements and the solid line a linear fit to the plotted data and the axis in FIGS. 12A-12D are in units of parts-per-billion (ppb) by volume. Ammonia concentrations were determined by IC and for the dry samplers, ammonia was extracted from the collection material with DI water and the resultant solution subjected to IC to determine ammonia concentrations.

Figure 12A:
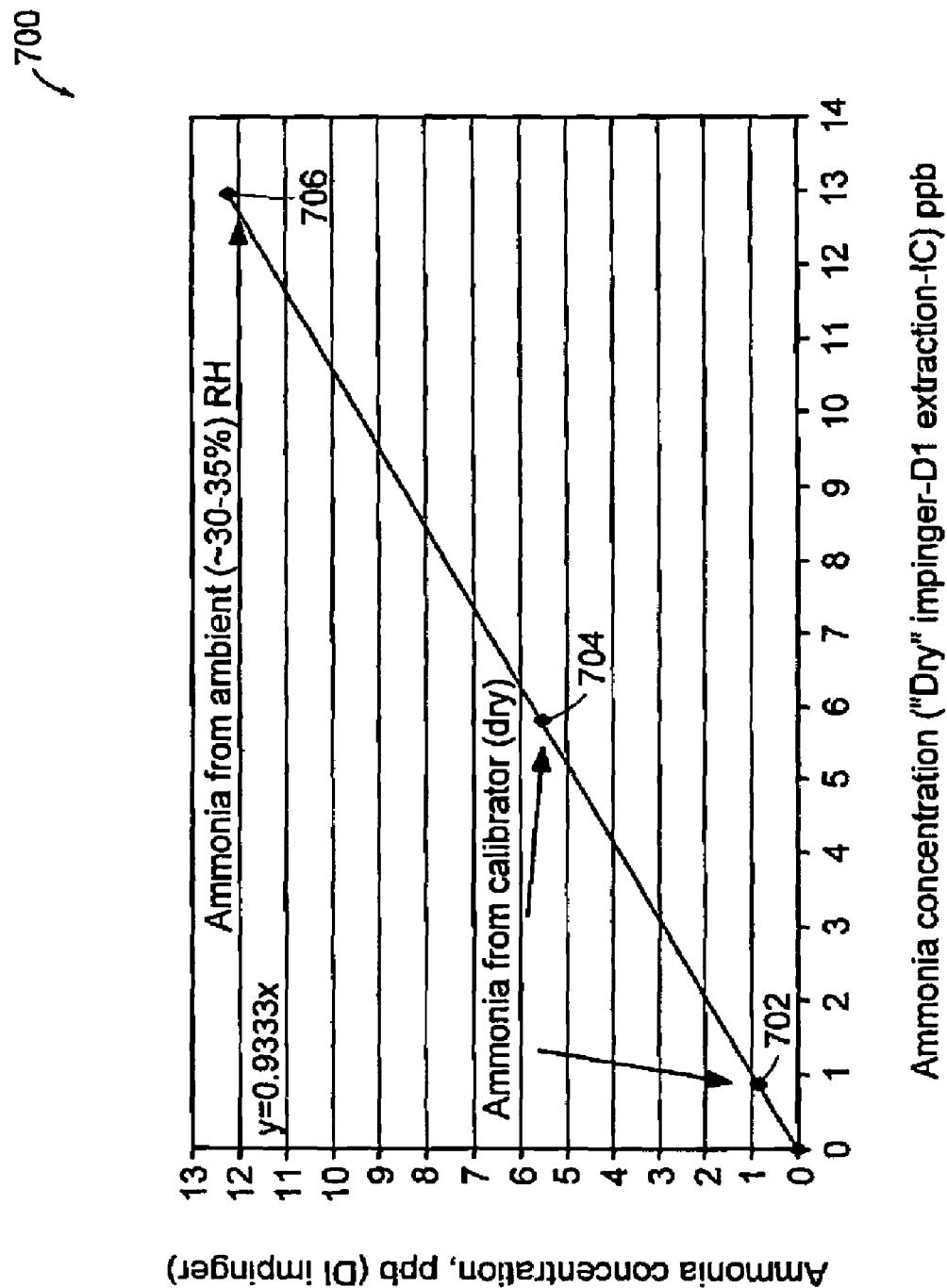
FIGS. 12A-12D compare measurements of ammonia concentration in an air stream determined using a deionized (DI) water wet impinger to those obtained using various embodiments of a dry sampler in accordance with the present invention.

The data in FIG. 12A is a plot 700 comparing ammonia concentrations as determined by a wet impinger (y-axis values) and a dry sampler (x-axis values) using various embodiments of active sampling. The active dry sampling (ADS) data is an average of measurements obtained using various flow rates to the dry sampler: 1 standard liters-per-minute (lpm) for four hours; 2 lpm for two hours; and 3 lpm for one hour. The first two data points 702, 704 represent ammonia concentration measurements of dry air from a calibrator, and the third data point 706 represents ammonia concentration measurements of ambient room air having a relative humidity (RH) of about 30-35%. The slope of the linear fit to the data in FIG. 12A was about 0.93. The data plotted in FIG. 12A is tabulated in Table 4.

TABLE 2

| Batch of pads #1 | Time delay (days) | Concentration (mg/L)- Room temp. storage. | Concentration (mg/L)- Storage was in the fridge. |
|---|---|---|---|
| stack of pads in one container | 0 | 0.004 | 0.004 |
| | 2.8 | 0.002 | 0.003 |
| | 2.8 | 0.008 | 0.008 |
| | 4.8 | 0.004 | 0.007 |
| | 5.8 | 0.001 | 0.003 |
| | 6.8 | 0.001 | 0.001 |
| | | Average 0.003 | Average 0.003 |

| Batch of pads #2 | Time delay (days) | Room Temp (mg/L) | Refrigerator (mg/L) |
|---|---|---|---|
| Separately in ind. containers | 1.8 | 0.002 | 0.001 |
| | 2.8 | 0.001 | 0.003 |
| | 3.8 | 0.003 | 0.002 |
| | | Average 0.003 | Average 0.002 |

TABLE 3

| Dry impinger | 1 day | 5 days |
|---|---|---|
| | Concentration, mg/L | |
| Blank | 0.005 | 0.008 |
| 1 | 0.004 | 0.003 |
| 2 | 0.004 | 0.002 |
| 3 | 0.003 | 0.002 |
| 4 | 0.003 | 0.004 |
| 5 | 0.002 | 0.004 |
| 6 | 0.002 | 0.004 |
| 7 | 0.003 | 0.005 |
| 8 | 0.002 | 0.002 |
| 9 | 0.003 | 0.003 |
| 10 | 0.003 | 0.003 |

TABLE 4

| Sample size | Wet Impinger | Dry sampler (ADS) |
|---|---|---|
| | Concentration, ppb | |
| 7 | 0.9 +− 0.1 | 0.8 +− 0.2 |
| 7 | 5.9 +− 0.2 | 5.3 +− 0.2 |
| 7 | 12.9(ambient) +/− 1.2 | 12.2(ambient) +/− 1.8 |

Figure 12B:
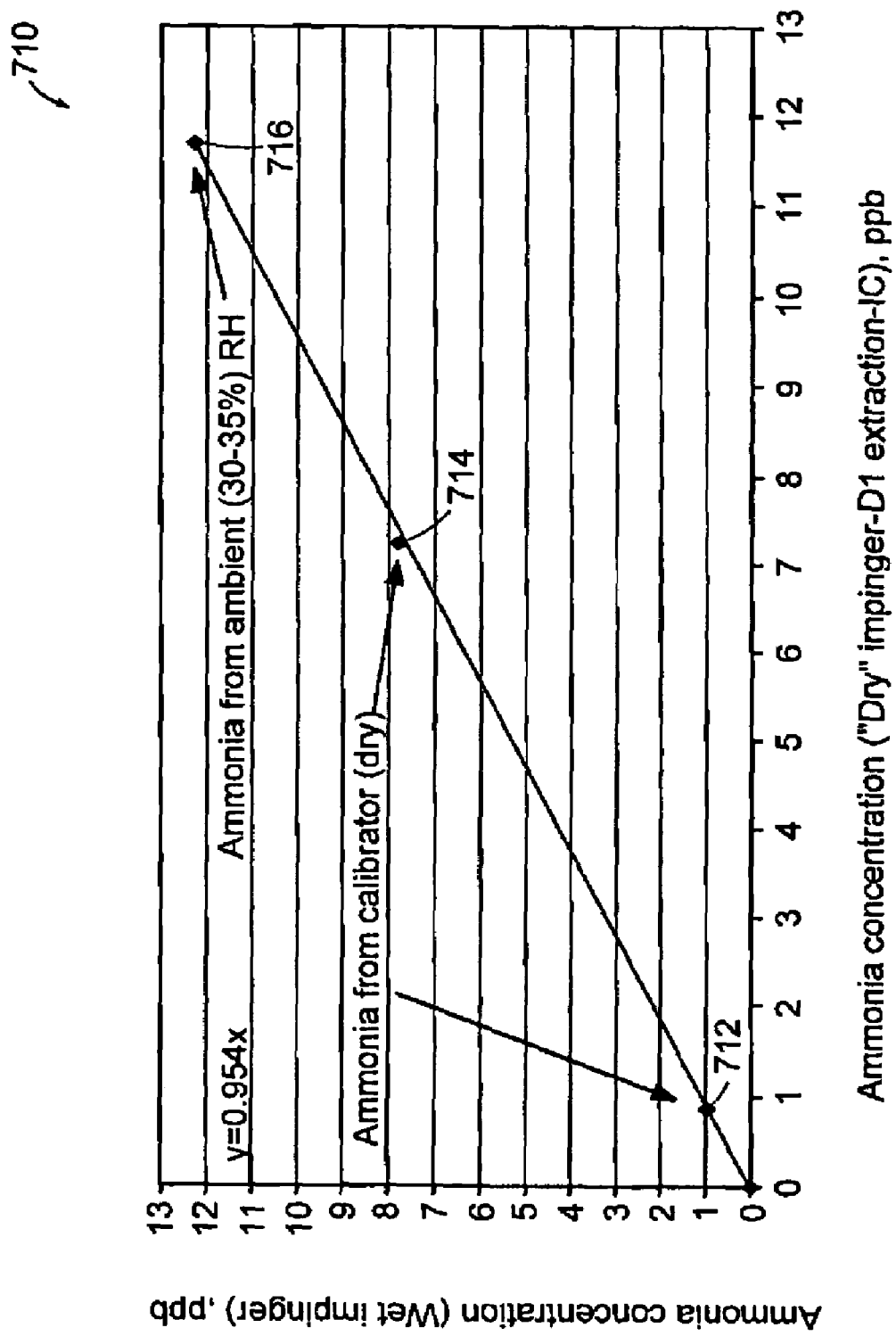

The data in FIG. 12B is a plot 710 comparing ammonia concentrations as determined by a wet impinger (y-axis values) and a dry sampler (x-axis values) using an embodiment of passive sampling. This passive dry sampling (PDS) data was obtained using sampling times sufficient to sample at least a total sample volume of 240 L. The first two data points 712, 714 represent ammonia concentration measurements of dry air from a calibrator, and the third data point 716 represents ammonia concentration measurements of ambient room air having a relative humidity (RH) of about 30-35%. The slope of the linear fit to the data in FIG. 12B was about 0.95.

Figure 12C:
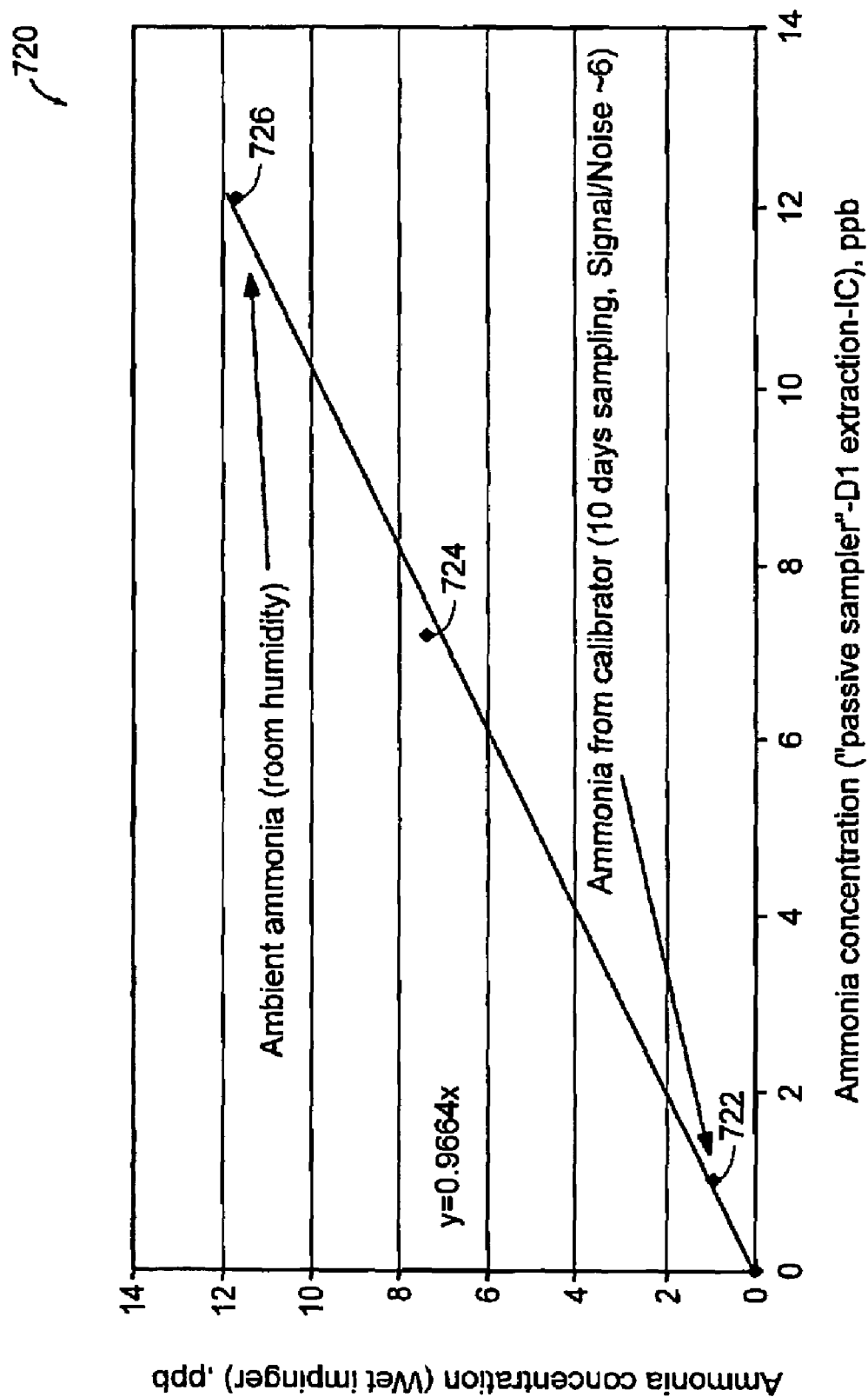

The data in FIG. 12C is a plot 720 comparing ammonia concentrations as determined by a wet impinger (y-axis values) and a dry sampler (x-axis values) using an embodiment of passive sampling. This PDS data was obtained using sampling time of ten days. The first two data points 722, 724 represent ammonia concentration measurements of dry air from a calibrator, and the third data point 726 represents ammonia concentration measurements of ambient room air. The slope of the linear fit to the data in FIG. 12C was about 0.97.

Figure 12D:
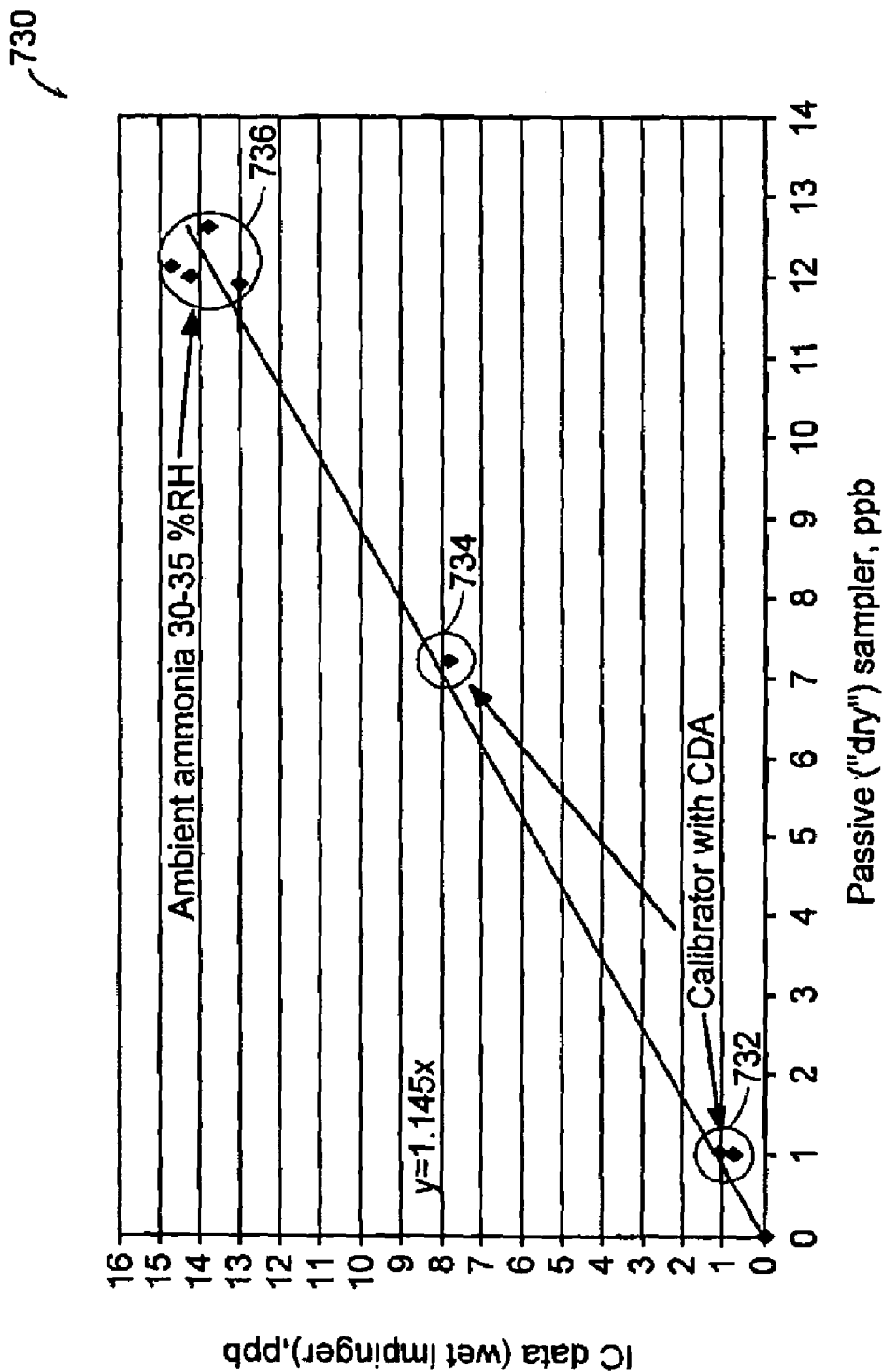

The data in FIG. 12D is a plot 730 comparing ammonia concentrations as determined by a wet impinger (y-axis values) and a dry sampler (x-axis values) using an embodiment of passive sampling. This PDS data was obtained using sampling times sufficient to sample at least a total sample volume of 240 L. The first two sets of data points 732, 734 represent ammonia concentration measurements of clean dry air from a calibrator, and the third data point 736 represents ammonia concentration measurements of ambient room air having a relative humidity (RH) of about 30-35%. The slope of the linear fit to the data in FIG. 12D was about 1.14.

The results of further comparisons of ammonia concentration measurements obtained using traditional DI water wet impingers to those obtained using various embodiments of dry sampler and dry sampler system configurations of the present invention are given in Tables 5-10 below.

TABLE 5

Cleanroom Ambient (RH~35%), Ammonia Concentration

| N | Dry Sampler, Active Sampling Configuration - IC analysis (ppbV) | Wet Impinger - IC analysis (ppbV) |
|---|---|---|
| 1 | 12.1 | 13.1 |
| 2 | 12.7 | 13.7 |
| 3 | 14.8 | 14.3 |
| 4 | 12.8 | 11.0 |
| 5 | 11.9 | 10.1 |
| 6 | 13.4 | 11.5 |
| 7 | 9.6 | 8.3 |
| 8 | 10.5 | 8.2 |
| 9 | 13.6 | 15.5 |
| 10 | 18.6 | 18.6 |
| 11 | 12.8 | 12.1 |
| 12 | 10.7 | 9.9 |
| 13 | 12.0 | 10.4 |
| 14 | 11.1 | 9.0 |
| 15 | 11.6 | 9.4 |
| 16 | 11.2 | 9.4 |
| Average | 12.5 | 11.5 |
| Sigma | 2.1 | 2.9 |
| +-%, 1 sigma | 17% | 25% |
| Bias | 8% | |

TABLE 6

About 5 ppbV Calibrator output with CDA, Ammonia Concentration

| N | Dry Sampler, Active Sampling Configuration - IC analysis (ppbV) | Wet Impinger - IC analysis (ppbV) |
|---|---|---|
| 1 | 5.2 | 5.0 |
| 2 | 5.5 | 5.1 |
| 3 | 5.5 | 5.7 |
| 4 | 5.0 | 6.4 |
| 5 | 5.1 | 5.8 |
| 6 | 5.5 | 6.8 |
| 7 | 5.1 | 5.5 |
| Average | 5.3 | 5.8 |
| Sigma | 0.2 | 0.7 |
| +-%, 1 sigma | 4% | 11% |
| Bias | -8% | |

TABLE 7

About 1 ppbV Calibrator output with CDA, ammonia concentration

| N | Dry Sampler, Active Sampling concentrations | Wet Impinger - Concentrations |
|---|---|---|
| 1 | Ppb | ppb |
| 2 | 1.2 | 1.1 |
| 3 | 0.9 | 1.1 |
| 4 | 2.1 | 1.7 |

TABLE 7-continued

About 1 ppbV Calibrator output with CDA, ammonia concentration

| N | Dry Sampler, Active Sampling concentrations | Wet Impinger - Concentrations |
|---|---|---|
| 5 | 1.0 | 1.1 |
| 6 | 0.8 | 0.7 |
| 7 | 0.8 | 0.7 |
| 8 | 1.7 | 1.1 |
| 9 | 0.8 | 0.5 |
| 10 | 0.6 | 0.4 |
| 11 | 0.7 | |
| 12 | 0.8 | 0.6 |
| 13 | 0.6 | 0.6 |
| 14 | 0.8 | 0.6 |
| 15 | 0.5 | 0.5 |
| Average | 0.9 | 0.8 |
| Sigma | 0.4 | 0.4 |
| +-%, 1 sigma | 47% | 0.5 |
| Bias | 18% | |

TABLE 8

Clean room ambient RH~35%, 21° C. Ammonia concentration

| Wet Impinger (ppbV) | Dry Sampler - Ammonia concentration (ppbV) | Sampling time days |
|---|---|---|
| 13.1 | | |
| 13.7 | | |
| 14.3 | 12.3 | 6 |
| 14.7 | 13.0 | 6 |
| 10.1 | 12.4 | 6 |
| 11.5 | | |
| 8.3 | | |
| 8.2 | | |
| 11.6 | | |
| 11.7 | 12.6 | 7% bias vs. wet impinger |

TABLE 9

Challenge from VICI calibrator, CDA-make-up gas

| Wet Impinger (ppbV) | Dry Sampler - Ammonia concentration (ppbV) | Sampling time days |
|---|---|---|
| 8.6 | 6.90 | 4 |
| 8.4 | 7.10 | 4 |
| 7.8 | 6.6 | 4 |
| 6.8 | 7.8 | 4 |
| 7.6 | 7.8 | 4 |
| 7.8 | | |
| 7.8 | 7.2 | -8% bias vs. wet impinger |

TABLE 10

Challenge from VICI calibrator, CDA-make-up gas passive sampling configuration

| Wet Impinger (ppbV) | Dry Sampler - Ammonia concentration (ppbV) | Sampling time days |
|---|---|---|
| 0.7 | calibrator | |
| 1.2 | | |

TABLE 10-continued

Challenge from VICI calibrator, CDA-make-up gas passive sampling configuration

| Wet Impinger (ppbV) | Dry Sampler - Ammonia concentration (ppbV) | Sampling time days |
|---|---|---|
| | 0.9 | 9 |
| 1.1 | 1.0 | 9 |
| 0.7 | 1.1 | 9 |
| 0.9 | | |
| 1.1 | | |
| 0.5 | | |
| 0.9 | 1.00 | 14% bias vs. wet impinger |

Figure 13A:
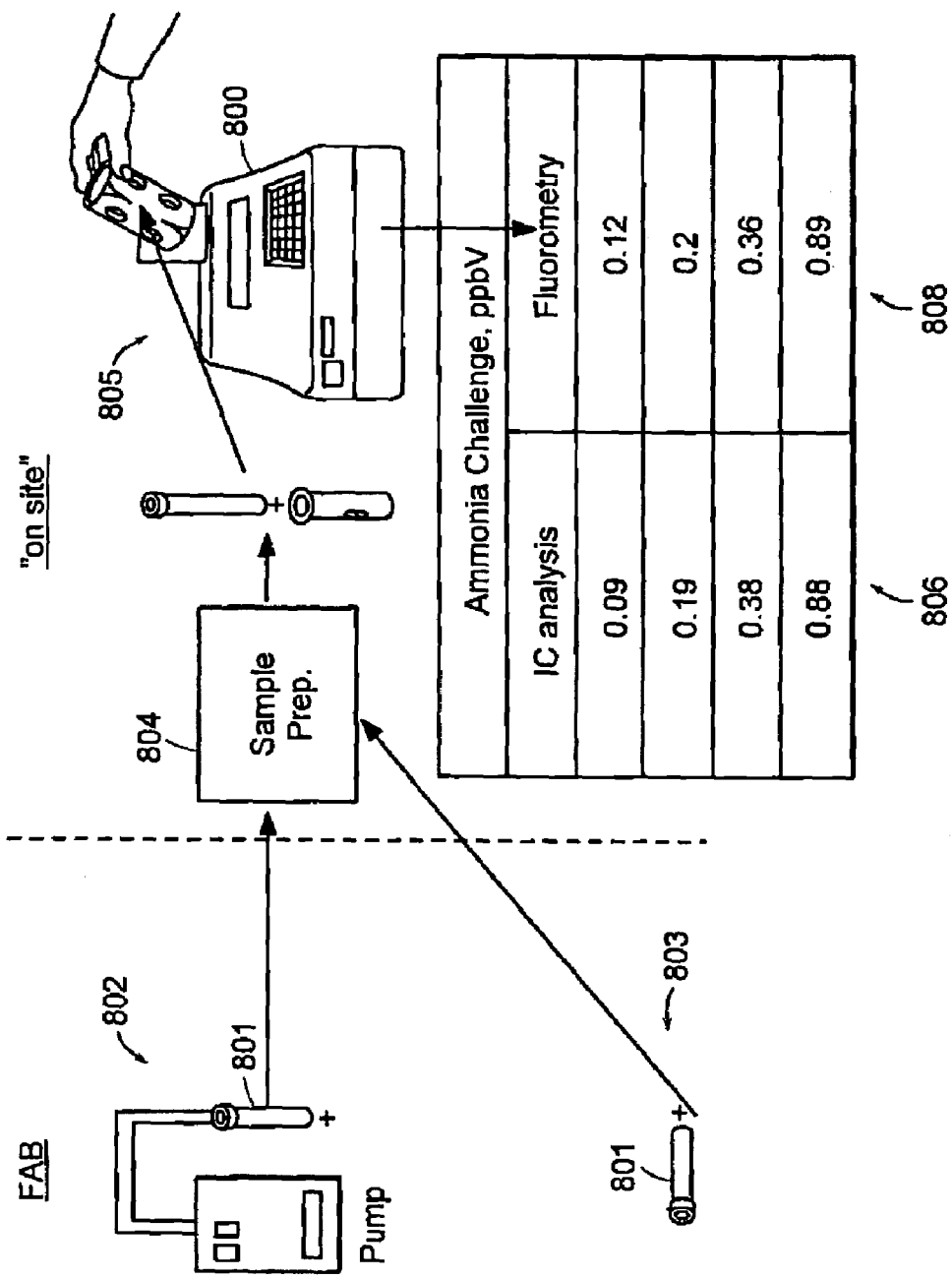
FIGS. 13A and 13B schematically illustrate various embodiments of an "on-site" measurement of analyte concentration obtained from a dry sample in accordance with the present invention.
Figure 13B:
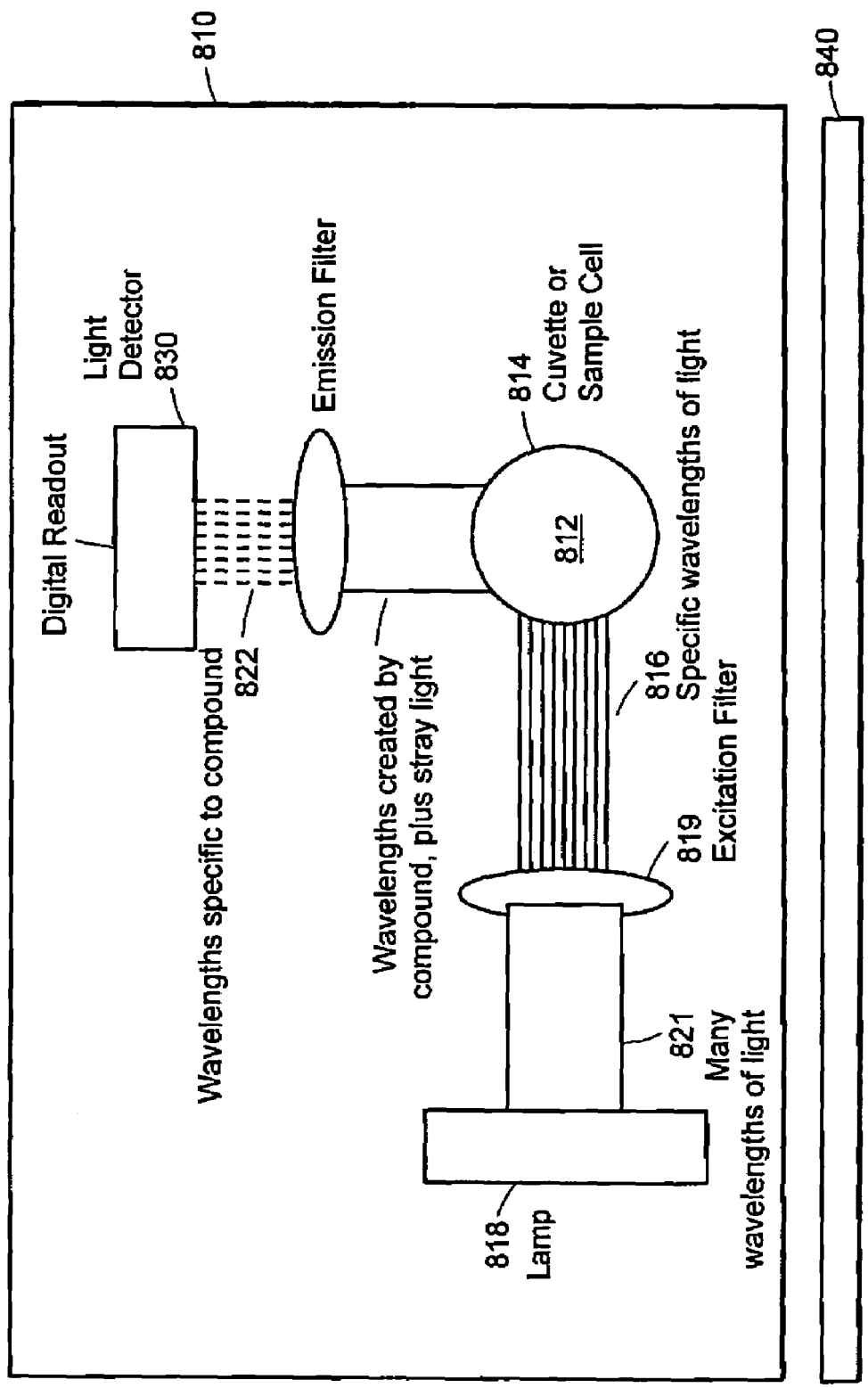

In various embodiments, the present invention provides methods of determining the concentration of a molecule of interest (analyte) using fluorometric analysis. In various embodiments, an analysis kit is provided including a dry sampler and a flourometer for measuring analyte concentration. FIG. 13A depicts one comparison of IC and fluorometric analysis and FIGS. 13A and 13B schematically depict one embodiment of on "on-site" measurement of analyte concentration using a fluorometer 800, 810. For example, one or more dry samplers 801 can be configured to sample in an active sampling configuration 802, passive sampling configuration 803 (e.g., by diffusion), or both. After a sampling time, the collection material is prepared for analysis 804, for example, by IC, fluorometry 805, etc. Results of a comparison of an IC analysis 806 and a fluorometric analysis 808 of a sample are also shown in FIG. 13A.

In various embodiments, molecules of interest are extracted from the collection material of the dry sampler and complexed with a suitable dye, if needed, for fluorometric analysis. This solution 812 is placed in a cuvette or sample cell 814 and irradiated with excitation light 816 from a source of excitation light 818, which can be specific wave lengths selected by a filter 819 from a broader band of light 821. The excitation light excites the dye molecules to fluoresce and the emitted light 822, specific to the compound of interest, is detected by a detector 830, such as, for example, a photomultiplier tube (PMT). Preferably, the fluorometer 810 is portable such that it can be carried or used with a cart 840.

Figure 14:
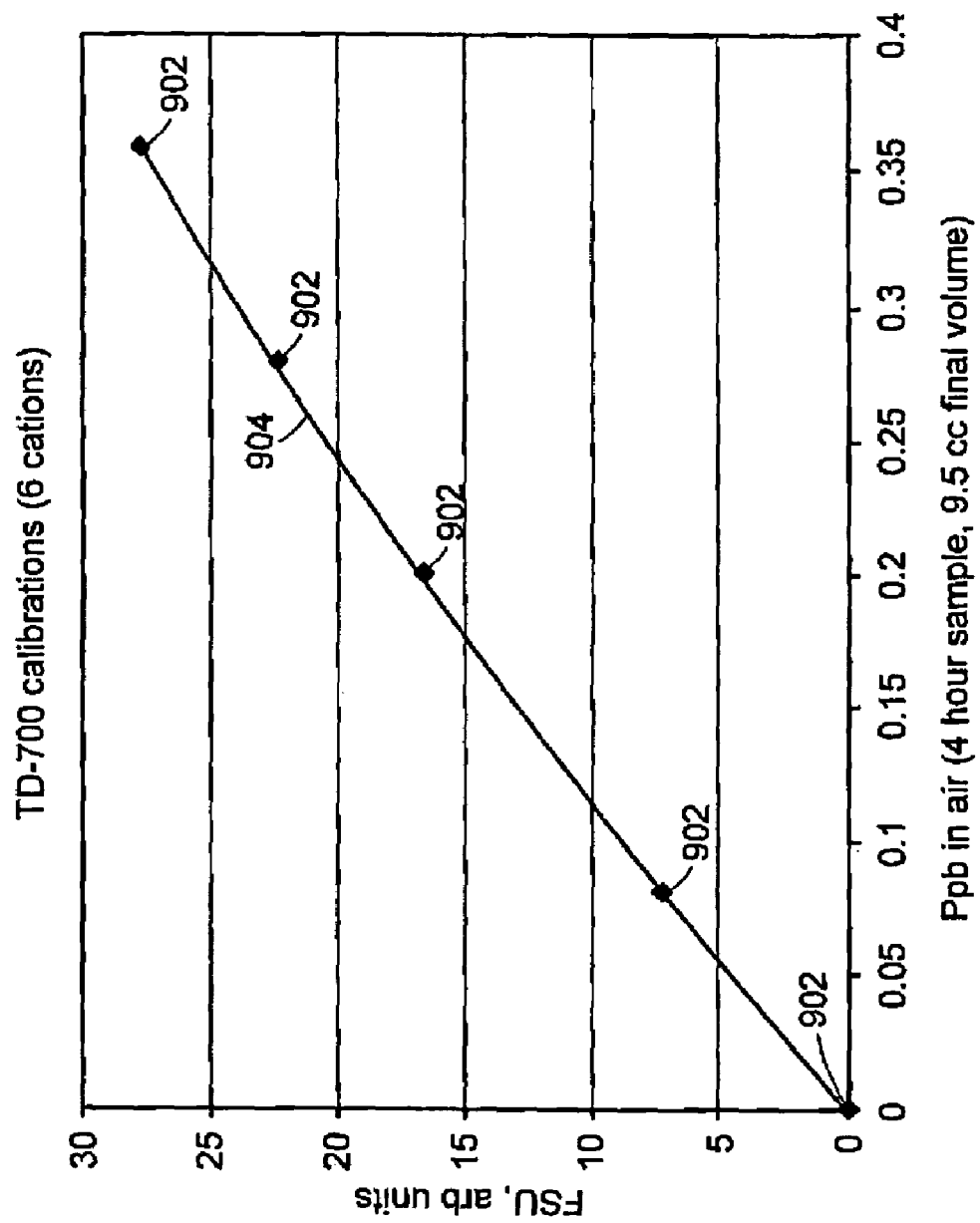
FIG. 14 is a fluorometer calibration curve for ammonia detection using an embodiment of a dry sample in accordance with the present invention.

FIG. 14 presents the results of several measurements (filled symbols 902) of known ammonia concentrations in air (x-axis values in units of ppbV) for a four hour active sampling (about 1 lpm flow rate) to produce a calibration curve (polynomial fit represented by solid line 904) for the fluorometer. The data in FIG. 14 is for a TD-700 Laboratory Fluorometer (Turner BioSystems, Inc. Sunnyvale, Calif 94085) using 500 nm excitation of about 3 ml of solution to which a dye of OPA was added. The y-axis represents the resultant fluorescence intensity observed in arbitrary units.

One challenge in development of a sampling device and approaches in embodiments using off-site analysis is to make sure that after a field sampling session the sample will "survive" travel back to the analytical lab. The data in Tables 11 and 12, respectively, are from two types of "travel" measurements conducted on various embodiments of dry samplers of the present invention using citric acid treated quartz fibrous media as a collection material. The measurement results shown in Table 11 are for a Type A measurement comprising: initial pre-loading of ammonia in the lab, "travel" and comparison of the results (this type of measurement can eliminate site specific issues AMC vs. airborne PM). The measurement results shown in Table 12 are for a Type-B test comprising: simultaneous sampling with wet impinger and dry sampler.

TABLE 11

| Sampling device | Location | TAT, days | Pre-loaded amount (no "travel") In mg/L (10 cc extraction) | After "travel". In mg/L (10 cc extraction) | Comments |
|---|---|---|---|---|---|
| 1" SS-"active" | Arizona (March) | 5 | 0.002 (unloaded blank) | 0.006 (unloaded blank) 0.004 (unloaded blank) | 2 different caps used (this design no longer tested). |
| ½" nylon housing-"active" | Arizona (April) | 6 | 0.095 | 0.092 | capped |
| ½" nylon housing-"active" | Arizona (May) | 5 | 0.004 | 0.006 | capped |
| ¾" polypropylene passive "Ogawa" | Arizona (May) | 5 | 0.023 | 0.025 | Were placed in Nalgene Bottles |

TABLE 12

| | Concentration ("dry" impinge) (ppb) | Concentration ("wet" impinge) (ppb) |
|---|---|---|
| Blank | 0.1 | 0.1 |
| CDA pre-filter | 1.8 | 2.9 |
| CDA pre-filter | 1.8 | 3 |
| Volume collected, L | 480 | 240 |

In the data of Table 12, the clean dry air (CDA) unit was purged for approximately four hours before sampling started. The inlet line was also purged for four hours at approximately 3 lpm and post filtered at approximately 0.5 lpm. Approximately one foot of tubing was attached to the sample port and the teflon manifold, the end of the manifold was open with a one foot length of tubing used as a diffusion barrier. Approximately 1 lpm excess flow was used. Additionally, two dry impingers were used in this measurement. Total flow from the pre-filter port was approximately 7.5 lpm. The inlet line to the CDA unit was brown in color with the following markings: "Parker Parflex pure air tubing, Pat6 ⅜" OD 350 wp, 029317 . . . ." The pumps used for the ADS configuration for the dry sampler were 4 L pumps, the flow rate was about 2 lpm and a sampling time of about 256 minutes.

Exemplary Wet Impinger

As previously discussed, wet impingers may be employed in embodiments of gas sampling unit 16 when it is desirable to compare results obtained using dry traps to results obtained using wet media. When wet impingers are employed in gas sampling unit 16, they may be connected in series as shown in FIG. 5A. Wet impingers 86 and 88 contain deionized water and are used for determining nitrogen containing acidic species in a gas sample. For example, nitric acid ($HNO_3$) may be measured as $NO_3^-$ ion and nitrous acid ($HNO_2$) measured as $NO_2^-$. In particular, wet impingers 86 and 88 are used to provide a result indicative of the difference between a measured value of ionic $NO_x$ and an actual value associated with atmospheric ionic $NO_x$. Atmospheric $NO_x$ represents the total of ionic and non-ionic $NO_x$ present in the air within a cleanroom, for example. In contrast, atmospheric ionic $NO_x$ ($NO_x^-$) is the total of nitric acid ($HNO_3$) measured as the $NO_3^-$ ion and nitrous acid ($HNO_2$) measured as $NO_2^-$. Virtual $NO_x^-$ represents the small fraction of non-ionic $NO_x$ solubilized by the series wet impingers 86 and 88 as ionic, respectively. Virtual $NO_x^-$ is a generated result caused by the interaction between atmospheric (non-ionic) $NO_x$ and water in the impingers. Virtual ionic $NO_x$ is formed by way of impingers 86 and 88 as follows:

  (1)

  (2)

  (3)

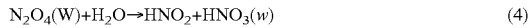  (4)

  (5)

  (6)

Note that in Equation 4 the acids dissociate as follows:

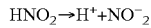

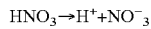

Thus, in passing through first wet impinger 86, a small fraction of atmospheric (non-ionic) $NO_x$ will be converted to virtual ionic $NO_x$ therein. The gas sample leaving first wet impinger 86 will contain almost the same amount and composition of atmospheric (non-ionic) $NO_x$ as the gas sample which entered it. Second wet impinger 88 will contain substantially the same amount of virtual $NO_x$ (i.e. the amount of ionic $NO_x$ that was generated from conversion of non-ionic $NO_x$ in the impinger) as was measured in first wet impinger 86. In contrast, the actual amounts of atmospheric (ionic) $NO_x$ will be effectively (i.e. substantially 99%) retained by the first wet impinger 86. Subtracting the measured amount of virtual $NO_x$ from the amount of ionic $NO_x$ retained in first impinger 86 produces a result indicative of the amount of atmospheric (ionic) $NO_x$ that was present in the sampled gas volume.

Exemplary Tenax Trap

First Tenax trap 90 and second Tenax trap 92 are used to retain non-acids and non-bases which typically consist of condensables, organic compounds, and refractory compounds. Refractory compounds are typically a non-volatile residue left from a photochemical reaction. Tenax traps 90, 92 may be custom fabricated for use in gas sampling unit 16 or they may be purchased as an off-the-shelf item. By way of example, an embodiment of gas sampling unit 16 employs Perkin Elmer Supelco Tenax traps.

Exemplary Controller

Figure 15:
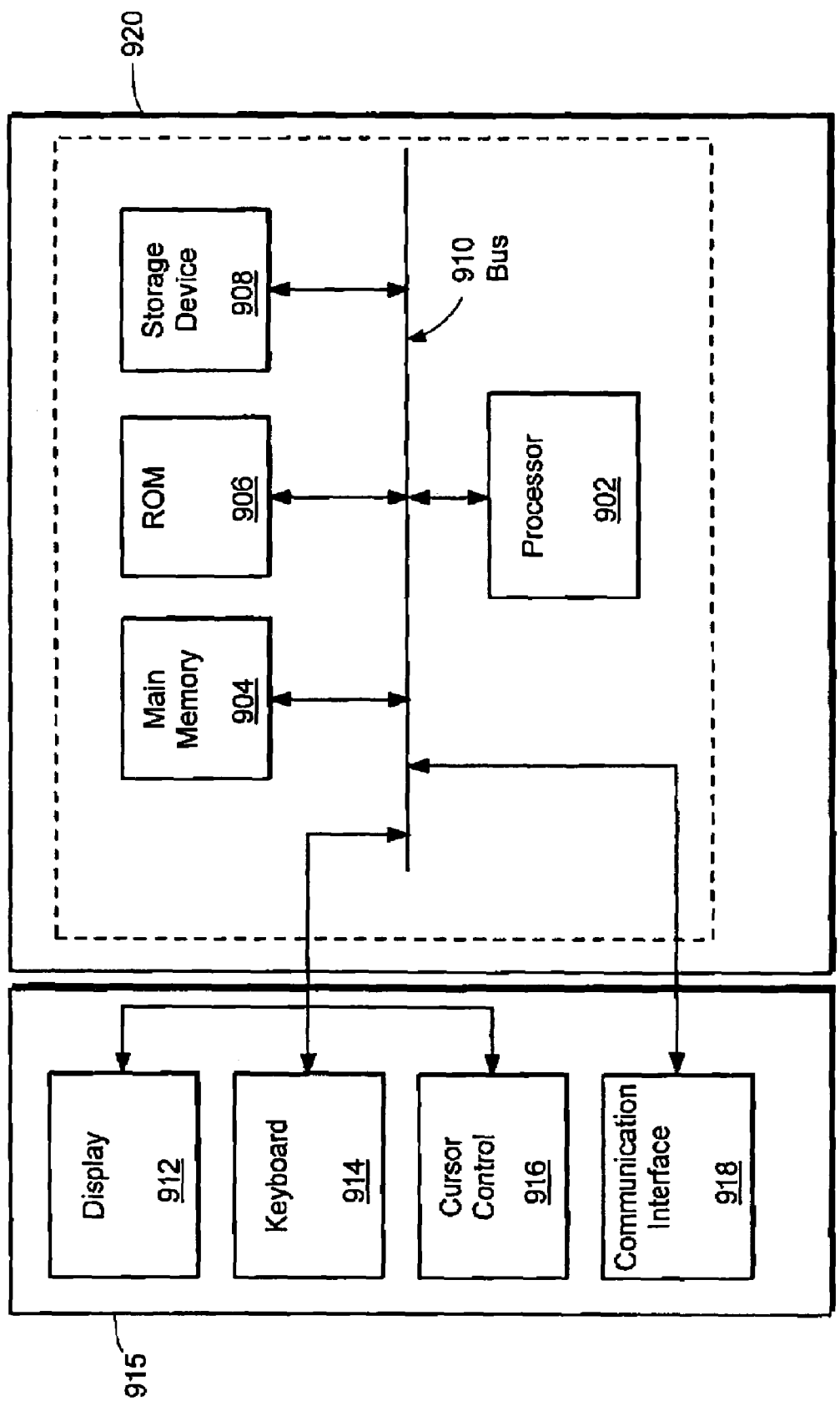
FIG. 15 illustrates a schematic representation of a controller used in embodiments of the invention.

Embodiments of gas sampling unit 16 may further include a controller for operating components such as solid state timer 114, vacuum pump 112, pressure regulator 102, computer controllable entry and exhaust manifolds, computer controllable pre-purge bypass valves, data displays, network interfaces, and the like. FIG. 15 illustrates an embodiment of a controller board 920 which can be a dedicated processor or can be in the form of a general-purpose computer that executes machine-readable instructions, or function-executable code, for performing control of gas sampling unit 16. The exemplary controller board 920 includes a processor 902, main memory 904, read only memory (ROM) 906, storage device 908, bus 910. The sampling unit can have an external port to communicate through computer interface 918 of external system 915 such that a user can retrieve and display data from the sampling unit or program the internal processor 902 using the display 912, keyboard 914, cursor control 916, and communication interface 918.

The processor 902 may be any type of conventional processing device that interprets and executes instructions. Main memory 904 may be a random access memory (RAM) or a similar dynamic storage device. Main memory 904 stores information and instructions to be executed by processor 902. Main memory 904 may also be used for storing temporary variables or other intermediate information during execution of instructions by processor 902. ROM 906 stores static information and instructions for processor 902. It will be appreciated that ROM 906 may be replaced with some other type of static storage device. The data storage device 908 may include any type of magnetic or optical media and its corresponding interfaces and operational hardware. Data storage device 908 stores information and instructions for use by processor 902. Bus 910 includes a set of hardware lines (conductors, optical fibers, or the like) that allow for data transfer among the components of controller 920 as well as external system 915.

The display device 912 of external system 915 may be a cathode ray tube (CRT), liquid crystal display (LCD) or the like, for displaying information to a user. The keyboard 914 and cursor control 916 allow the user to interact with the controller 920. In alternative embodiments, the keyboard 914 may be replaced with a touch pad having function specific keys. The cursor control 916 may be, for example, a mouse. In an alternative configuration, the keyboard 914 and cursor control 916 can be replaced with a microphone and voice recognition means to enable the user to interact with the controller 920.

Communication interface 918 enables the controller 920 to communicate with other devices/systems via any communications medium. For example, communication interface 918 may include a modem, an Ethernet interface to a LAN (wired or wireless), or a printer interface. Alternatively, communication interface 918 can be any other interface that enables communication between the controller 920 and other devices or systems.

By way of example, a controller 920 consistent with the present invention provides a gas sampling unit 16 with the ability to communicate over network 22 while operating in a cleanroom 12. Alternatively, network 22 may convey signals to gas sampling unit 16 for remotely turning the unit on at a determined time and for remotely turning the unit off when a determined sampling interval has been concluded. In addition, controller 920 may be used to calibrate components within dry sampler 16. The controller 920 performs operations necessary to complete desired actions in response to processor 902 executing sequences of instructions contained in, for example, memory 904. Such instructions may be read into memory 904 from another computer-readable medium, such as a data storage device 908, or from another device via communication interface 918. Execution of the sequences of instructions contained in memory 904 causes processor 902 to perform a method for controlling gas sampling unit 16. Alternatively, hard-wired circuitry may be used in place of or in combination with software instructions to implement the present invention. Thus, the present invention is not limited to any specific combination of hardware circuitry and software.

The processor 902 can include an internal clock and battery as well as a temperature sensor. The temperature sensor can record temperature excursions of the unit 16 during use and transport to indicate whether samples have been compromised or damaged during use or unit transport.

In preferred emodiments, the processor 902, or board 920, can be connected to various devices within the unit 16 to control their operation or to record or use data to perform various control or diagnostic functions. In a preferred embodiment, pressure sensors, which can be positioned at the entry and/or exit manifolds, for example, can determine if the valves, feed lines or fittings are not working or are blocked. Flow meters can be located at each of the fittings 96A-96E, for example, to measure and record the total volume of gas flowing through each sampling element 82, 84, 86, 88, 90, 92. The processor 902 (or board 920) can also send control signals to control value that an include individual values for each sampling element as well as values 54,56. The processor 902 can also control temperature controllers, such as Peltier coolers, that can control the temperature of the Tenax traps 90, 92 to increase their capacity.

Another preferred embodiment uses a control source located in the sampling unit that emits a contaminant not found in the units ambient conditions (such as a carbon isotape) in order to verify that there are no leaks that will affect the measurement. The board 920 can also control cooling pan and pump operation.

Exemplary Method for Using Gas Sampling Unit

Figure 16A:
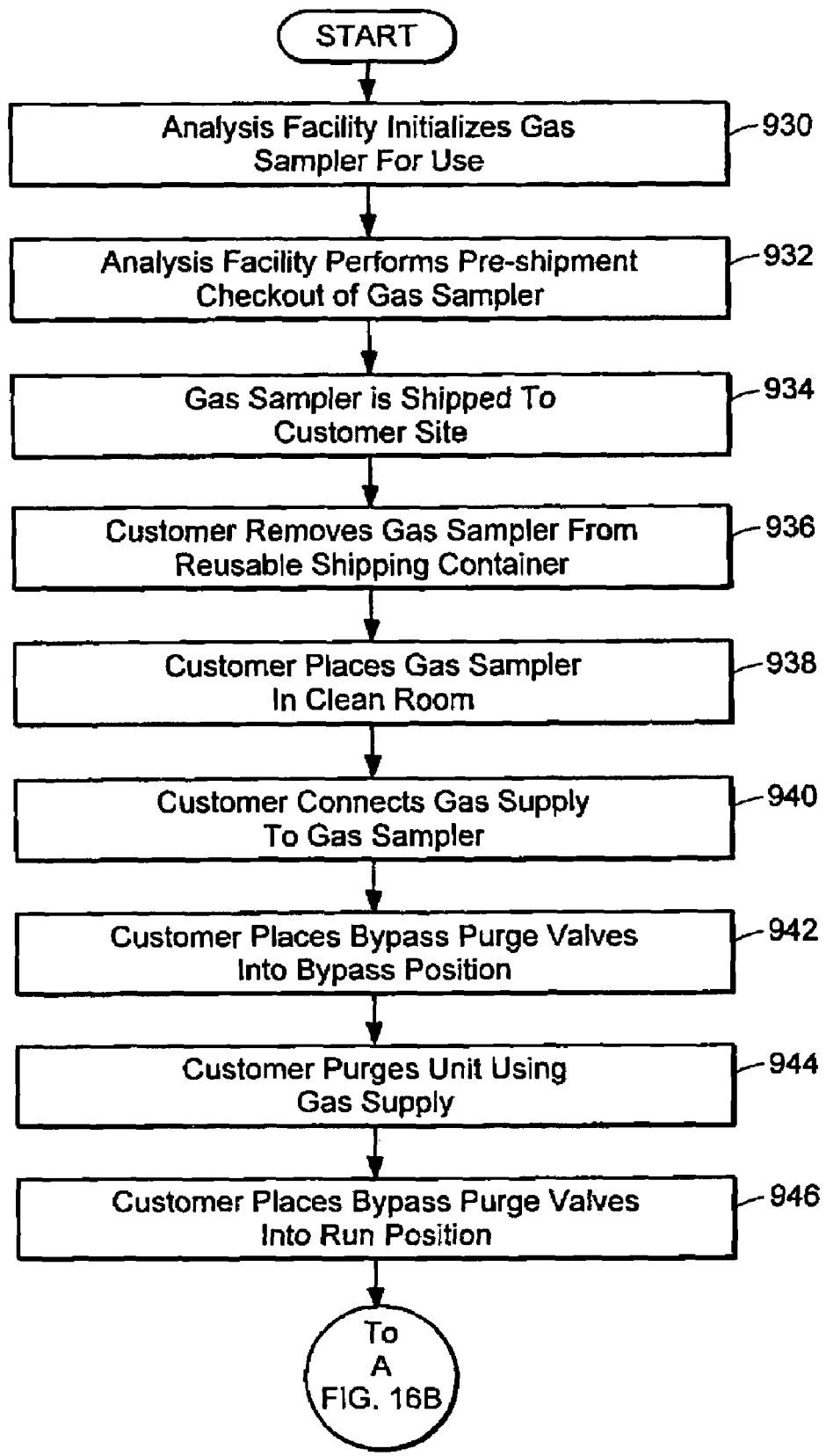
FIGS. 16A-16D contain an exemplary flow diagram illustrating a method for using a system to acquire contaminant data and for processing the acquired data to obtain a result.
Figure 16B:
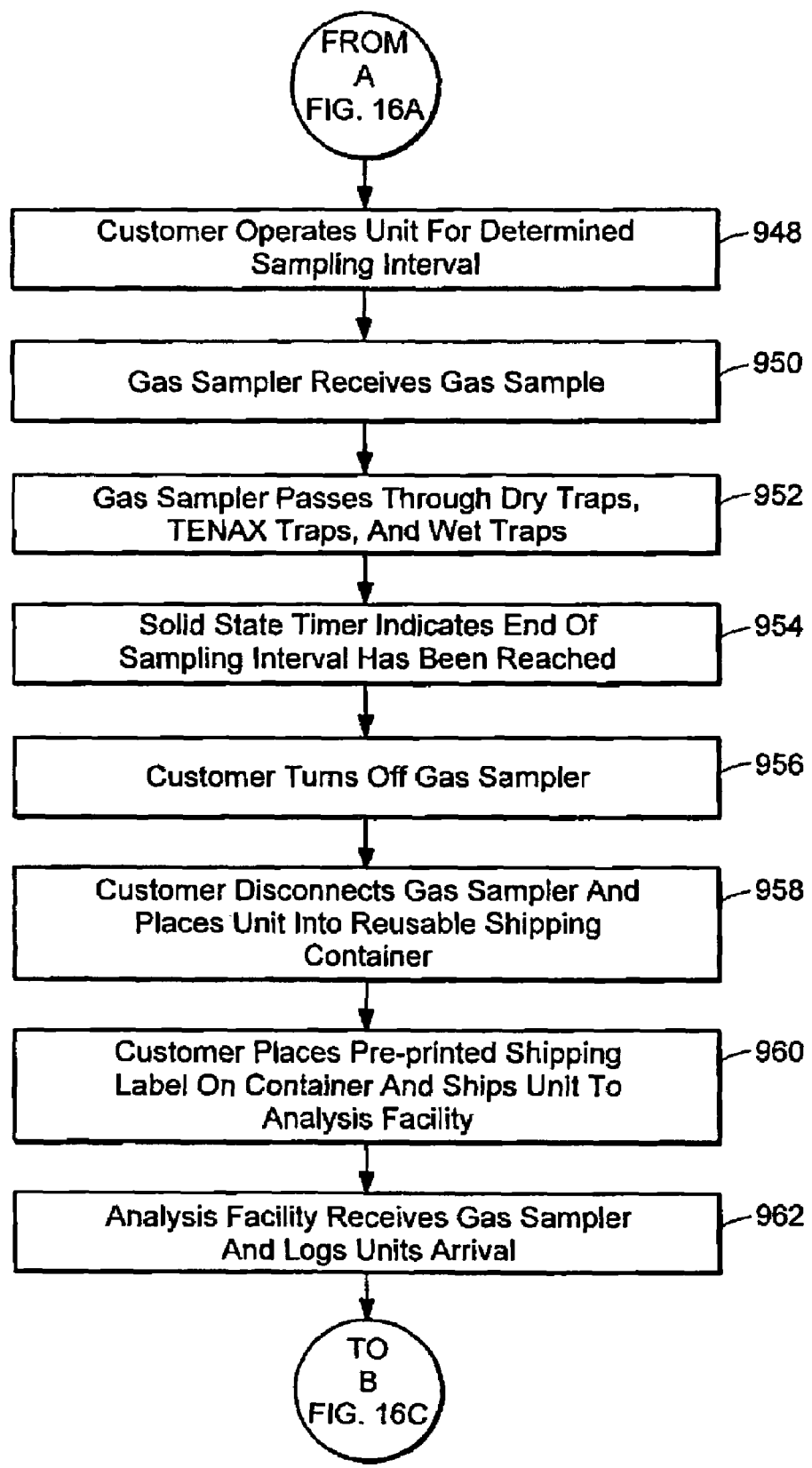
Figure 16C:
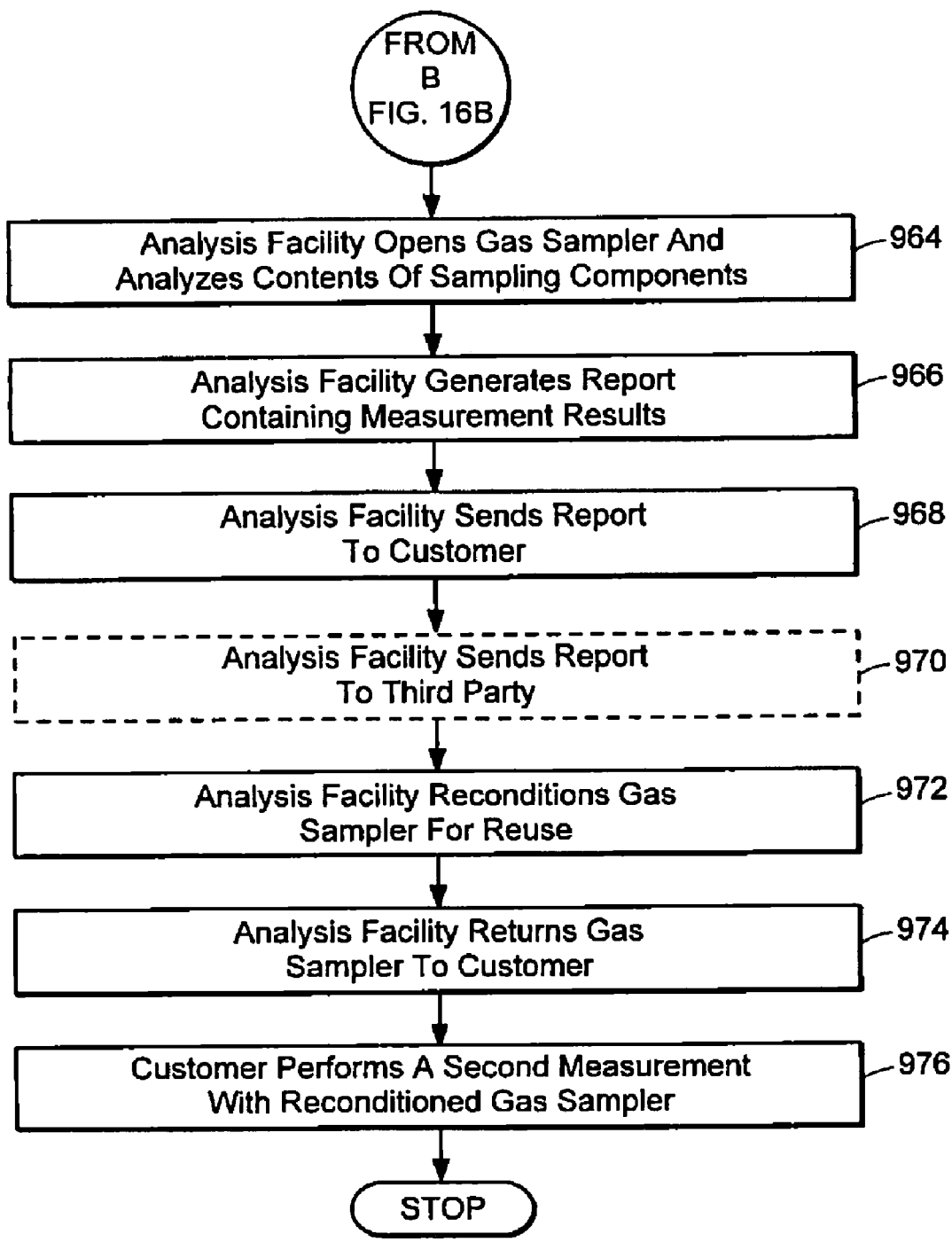

FIGS. 16A-16C contain flowcharts illustrating an exemplary method for using gas sampling unit 16 for measuring contaminants present in a cleanroom 12. In FIG. 16A, the method begins when analysis facility 18 initializes gas sampling unit 16 for making contamination measurements (per step 930). Next, a pre-shipment checkout/test of gas sampling unit 16 may be performed by analysis facility 18 (per step 932). The gas sampling unit 16 is shipped to a customer site via common carrier (per step 934). Upon receipt, the customer removes gas sampling unit 16 from a reusable shipping container used by analysis facility 18 (per step 936). The customer places gas sampling unit 16 in a cleanroom environment (per step 938) and connects the unit to a gas supply (per step 940). Embodiments of sampling unit 16 are designed to be used by relatively unskilled workers and therefore do not require specialized training procedures. Next, the customer places first and second bypass purge valves 54, 56 in bypass position (per step 942) to purge gas sampling unit 16 using the cleanroom 12 gas supply line (per step 944). The customer then places first and second bypass purge valves 54,56 into run position (per step 946) and allows the gas sampling unit 16 to operate for a determined sampling interval (per step 948, FIG. 16B). Gas sampling unit 16 may be operated anywhere from a few hours to several weeks depending on the types of contaminant measurements being made.

Gas sampling unit 16 receives a gas sample (per step 950) and passes the sample through dry traps 82,84, Tenax traps 90,92 and wet traps 86,88 (per step 952). Solid state timer 114 indicates to the customer that the end of the sampling interval has been reached (per step 954). The customer turns off gas sampling unit 16 in response to the readout of solid state timer 114; or alternatively, gas sampling unit 16 may automatically turn off when the end of the desired sampling interval is reached (per step 956). The customer disconnects gas sampling unit 16 from the gas supply and places the unit into the reusable shipping container (per step 958). The customer places a pre-printed return shipping label on the container and ships the unit back to analysis facility 18 (per step 960).

Analysis facility 18 receives gas sampling unit 16 and logs the unit's arrival into its inventory management system (per step 962). The dry sampler is opened by a technician and the contents of the sampling components are analyzed using methods known in the art (per step 964, FIG. 16C). The analysis facility 18 generates a report containing results of measurements taken by gas sampling unit 16 while installed at the customer site (per step 966). The report is sent to the customer via hardcopy and/or in electronic format, such as email (per step 968). In addition, analysis facility 18 may send a copy of the results to a third party, such as a certification or standards setting organization or government entity, having some type of oversight authority for the customer site (per step 970). An alternative embodiment of analysis facility 18 can maintain a web site containing the results of sampling data taken by gas sampling unit 16. Secure access by way of passwords or other security means known in the art may be used to prevent unauthorized access to data on the web site.

The analysis facility reconditions gas sampling unit 16 so that it can be reused by a customer for taking additional contamination measurements (per step 972). The analysis facility returns the sampling system to the customer (per step 974) and the customer uses gas sampling unit 16 to perform additional contamination measurements (per step 976).

Figure 16D:
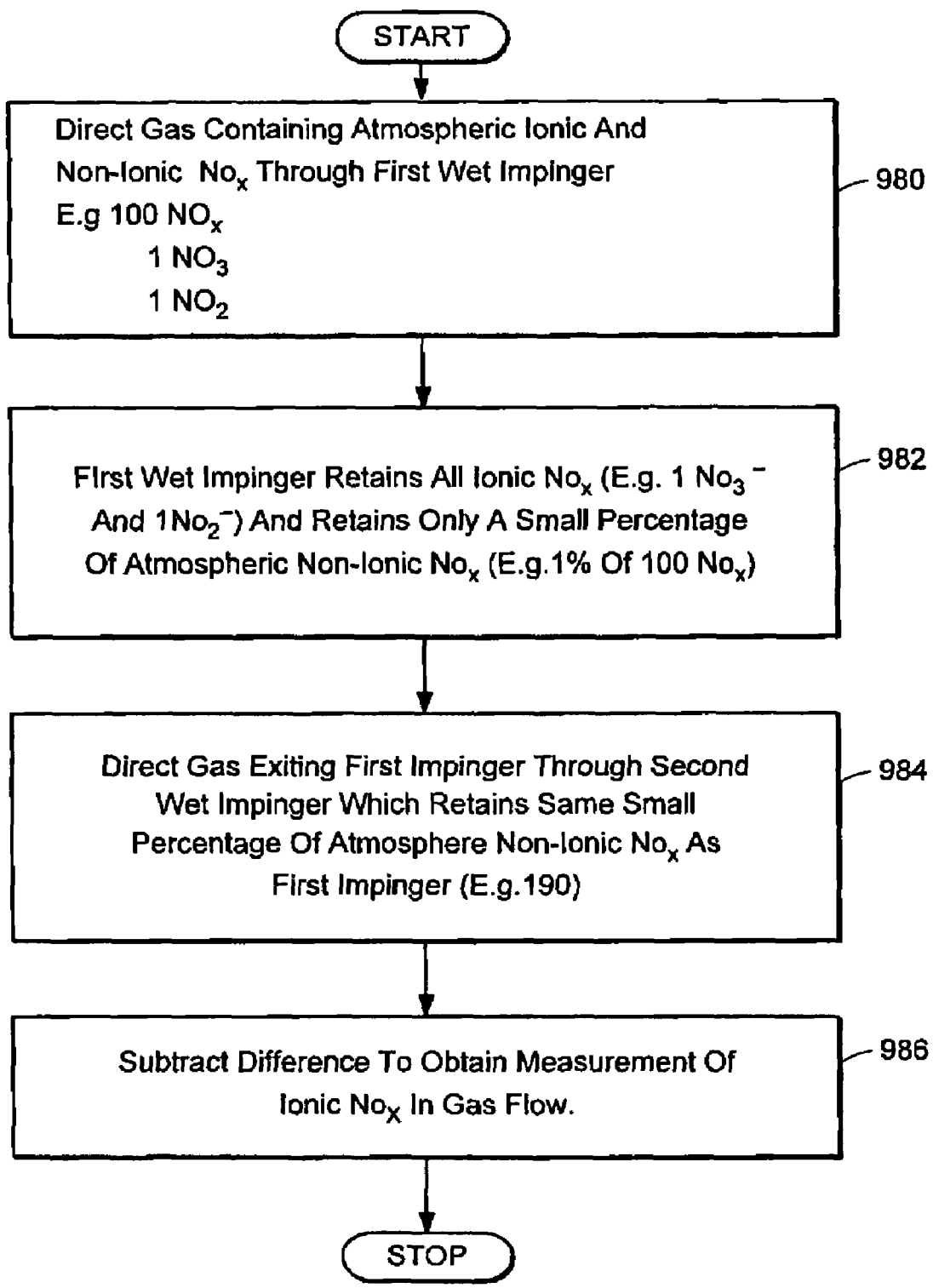

FIG. 16D illustrates an exemplary method for measuring the level of ionic $NO_x$ in a gas sample using an embodiment in which a first impinger and a second impinger are arranged in series. Note that the first and second impinger can also be used in parallel to provide two separate measurements. A gas sample containing atmospheric $NO_x$ is directed through a first wet impinger (step 980). By way of example, if the gases are thought of as balls, there are 100 balls of $NO_x$, one ball of $NO_3$ and one ball of $NO_2$ entering first wet impinger. The first wet impinger retains all ionic $NO_x$ arid retains only a small percentage of atmospheric $NO_x$ (step 982). Using the ball example, the first impinger will retain one $NO_3$-ball and one $NO_2$-ball and will only retain one $NO_x$ ball. The gas is then directed from first wet impinger through second wet impinger which retains the same small percentage of atmospheric $NO_x$ as was retained by the first wet impinger (step 984). For example, one $NO_x$ ball would be retained. The retained $NO_x$ in the second impinger is subtracted from the retained $NO_x$ in the first impinger to get the amount of ionic $NO_x$ in the gas flow (step 986).

Figure 17A:
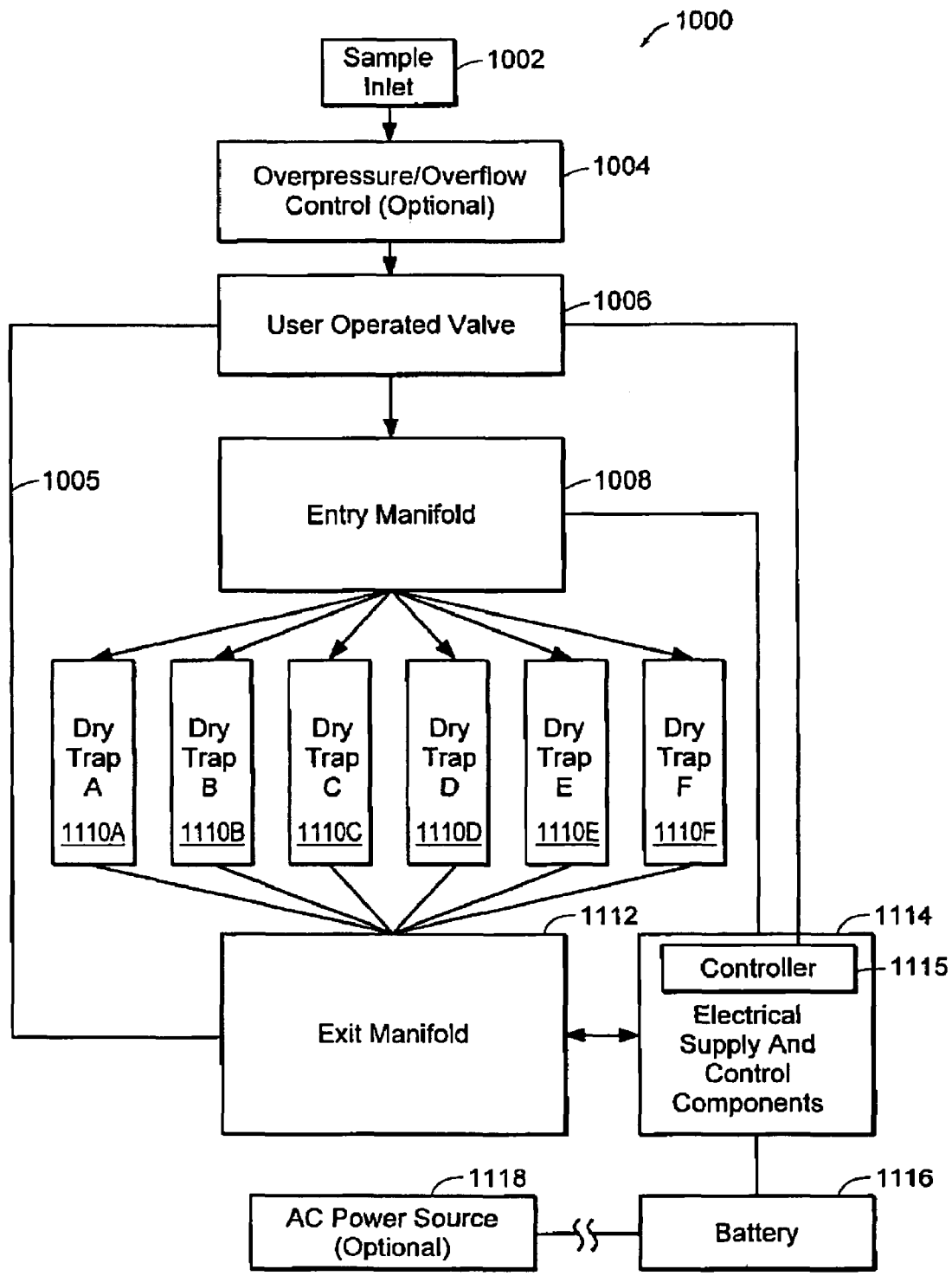
FIG. 17A illustrates a schematic representation for a handheld embodiment of a gas sampling system.

Embodiments of the gas sampling unit may take many forms. For example, a first alternative embodiment of a gas sampling unit may take the form of a handheld gas sampling unit 1000. FIG. 17A illustrates a schematic representation of components that can be used in a handheld unit 1000. For example, handheld unit 1000 may include a sample inlet 1002, an overpressure/overflow control 1004, one or more user operated valves 1006, an entry manifold 1008, one or more dry traps 1110, an exit manifold 1112, electrical supply and control components 1114, a battery 1116 and an optional AC power source 1118.

Sample inlet 1002 can include a coupling capable of allowing a gas sample to pass therethrough. For example, sample inlet 1002 may include an NPT connector adapted to mateably receive a gas supply line. An optional overpressure/overflow control 1004 may be inserted between sample inlet 1002 and user operated valves 1006 to prevent an overpressure or overflow condition within handheld unit 1000. User operated valves 1006 can be operated to allow passage of a gas sample into entry manifold 1008, or the valves 1006 can be operated to prevent passage of the gas sample. In addition, valves 1006 can be configured to cause a gas sample to flow directly to exit manifold 1112 via bypass channel 1005 without passing through entry manifold 1008 and or dry traps 1110A-F. Bypassing entry manifold 1008 is useful for purging the gas sample line prior to passing a gas sample through dry traps 1110A-F. In a preferred embodiment of handheld unit 1000, valves 1006 are operated by way of controller 1115 operating within electrical supply and control components 1114.

Entry manifold 1008 receives the gas sample and distributes it to dry traps 1110A-F. The embodiment illustrated in FIG. 17A includes six dry traps; however, handheld unit 1000 may operate with substantially any number of dry traps depending on the type and concentration of contaminants being measured. Exit manifold 1112 receives the gas sample that was distributed by entry manifold 1008 and generates a single output gas stream. The output gas stream can be coupled to a sample outlet connector located on the exterior of handheld unit 1000. The sample outlet connector facilitates gas passage through handheld unit 1000 without allowing the gas sample to be exhausted into the ambient environment in which handheld unit 1000 is operating.

Handheld unit 1000 may also include an electrical supply and control components subsystem 1114. The electrical subsystem can include a controller 1115, power regulation and distribution modules, alarm indicators, error sensors, cooling fans, and the like.

For example, in a preferred embodiment of handheld unit 1000, electrical subsystem 114 measures sample times, measures and controls flow rates, measures gas pressures, temperatures, and humidity levels, controls valves 1006, controls entry manifold 1008, controls exit manifold 1112, logs performance data, receives and logs user input data such as date, time, sampling location, and the operator's name. Using electrical subsystem 1114, handheld unit 1000 can be configured such that a user presses a single button to make measurements after connecting a gas line to the input of handheld unit 1000. The controller 1115 operating within handheld unit 1000 can facilitate preprogrammed operation by a user. For example, controller 1115 can be programmed to allow a gas sample to pass through only a subset of dry traps 1110A-F.

Handheld unit 1000 may further include an internal power source, such as battery 1116. Battery 1116 may consist of one or more replaceable batteries, such as disposable alkaline batteries or it may consist of a rechargeable battery, such as a lithium ion, nickel metal hydride, and the like. Handheld unit 1000 may also include a connector for coupling an external power source thereto such, as, for example, an AC power source.

FIG. 17B illustrates an exemplary embodiment of a handheld unit 1000 that includes some, or all, of the components illustrated in FIG. 17A. Handheld unit 1000 includes a case 1120 having an upper surface 1122 and a lower surface 1124 opposedly mounted from the upper surface 1122, a first side 1126 and a second side 1128 opposedly mounted from the first side 1126, a third side 1130 and a fourth side 1132 opposedly mounted from the third side 1130. Upper surface 1122 may include an ON/OFF switch 1134 for powering handheld unit 1000 on and for powering the unit off after a sampling interval is completed. An ON LED 1136 and OFF LED 1138 may be used for informing a user about the status of handheld unit 1000. A valve control button 1140 may be located on upper surface 1122 for letting a user place the handheld unit 1000 in a run mode or in a bypass/purge mode. Handheld unit 1000 can also include one or more displays for providing operational information to a user. For example, handheld unit 1000 can have a timer display 1142 for displaying a running time of the unit. A diagnostic display 1144 may provide information as to the unit's operational status, such as flow rates, gas sample temperature, valve status, and the like. Handheld unit 1000 also includes a gas sample inlet port 1148 and a gas sample exhaust port 1150.

Embodiments of handheld unit 1000 can also utilize a replaceable dry trap module 1154. Replaceable module 1154 can be inserted into housing 1120 by way of a dry trap receptacle 1152. Receptacle 1152 includes an opening, for example in first side 1126, into which the replaceable module 1154 is inserted. Once inserted into housing 1120, dry traps contained in replaceable module 1154 are positioned so that a gas sample passes therethrough to measure contaminants in the gas sample. A controller 1115 can be adapted to read measurement data from the dry traps for reporting to a user using results display 1146.

While embodiments of the sampling system described thus far employ a combination of dry traps, Tenax traps and wet impingers, other types of detectors can be employed. For example, embodiments can utilize sensors that change their output response when contaminants are detected. An example of a sensor having this type of characteristic is a surface acoustic wave (SAW) sensor. Sensors such as these can have surface coated materials that facilitate the retention of contaminants thereon. Contaminants retained on the detection surface of a sensor preferably form non-volatile residues which can subsequently be detected. Buildup of non-volatile residues on the detection surface may be representative of the concentration of molecular contamination in the airstream in the vicinity of the detection surface. These sensors can be used at input, or upstream, sampling locations, at output, or downstream, sampling locations, or at mid-point, or inter-stack, sampling locations with respect to filter systems operating in a cleanroom.

The actual formation rate of non-volatile residue onto the detection surfaces of an upstream and downstream detector not only depends on the varying molecular contamination concentrations in the respective airstreams, but also depends on other factors, such as temperature, humidity, and the amount of material previously formed onto the detection surfaces, all of which change over time, creating artifacts in the measured signals. For example, the rate non-volatile residue forms onto the upstream detection surface exposed to upstream air having a constant concentration of molecular contamination may change significantly over time. For example, a significant drop in the formation rate may result from a change in temperature or humidity. Also, a generally decreasing artifact in the formation rate may be observed due to changes in the detection surfaces over time caused by previously formed material.

Similar trends may be observed in the rate of non-volatile residue formation on a downstream, or post-filtering, detection surface. However, a generally decreasing artifact, similar to an artifact accumulating on an upstream detection surface typically appears at a later time in the measured formation rate on the downstream detection surface because the rate of material formation on the downstream detection surface is less than the formation rate on the upstream detection surface as long as a filter system is operating. Also, superimposed onto these artifacts for the downstream detector are changes in the concentration of molecular contamination in the airstream resulting from changes in filter efficiency.

Referring to FIG. 18A, a detector 1200, which may be used as upstream detector, mid-stack detector, or downstream detector, includes a detection surface 1202, which is exposed to an incoming air stream 1204 including molecular contamination 1206. In a presently preferred embodiment, detection surface 1202 is formed from a piezoelectric crystal 1208 and is configured as a mass microbalance resonator sensor, as described in W. D. Bowers et al., "A 200 MHz surface acoustic wave resonator mass microbalance," Rev. Sci. Instrum., Vol. 62, June 1991, which is herein incorporated by reference. The frequency of vibration is related to the way the crystal is cut and to the amount of mass formed on detection surface 1202. Leads 1210, 1212 are used to apply time-varying electrical signals to piezoelectric crystal 1208. Leads 1210, 1212 are also used to detect a shift in the resonant frequency of the detector. Alternatively, detector 1200 may be configured as a delay line, as described in H. Wohltjen et al., "Surface Acoustic Wave Probe for Chemical Analysis," Analytical Chemistry, Vol. 51, No. 9, pp. 1458-1475 (August 1979).

Even when detection surface 1202 is exposed to an air stream having a constant concentration of molecular contamination, the measured rate of change of formed non-volatile residue will vary depending on environmental conditions, e.g., temperature and humidity. The amount of deposited (formed) material will also depend on other parameters, e.g., the amount of material previously deposited onto the surface. The detectivity D(t) of a detection surface may depend on $$D(t) = K_1 \cdot S(T, RH, R, A(t)) \quad (1)$$

where, $K_1$ is a constant, S(T, RH, R, A(t)) is a "sticking coefficient" that depends on (among other things) the temperature (T), the relative humidity (RH), the reactivity (R) of the surface with the molecular contamination, and A(t) which is the effective surface area of the detection surface which decreases over time (t). The sticking coefficient (S) represents a probability that molecular contamination in the vicinity of the detection surface will condense from the gas-phase and adhere onto the detection surface.

Molecular contamination 1206 may simply condense from the gas-phase onto the surface of detector 1200 to form a non-volatile residue 1214. Also, selective adsorption of a particular class of molecular contamination may be achieved, e.g., by applying to the detection surface a thin film (coating) of a selectively adsorbing material. Thus, when exposed to molecular contamination, some of the molecular contamination may be adsorbed on the detection surface of the detector as a non-volatile reaction product residue 1216. The deposited non-volatile residue 1214 and non-volatile reaction product residue 1216 increase the mass on the detection surface that is measured as a resonant frequency shift.

The decrease in frequency following an increase in mass ($\Delta m$) of an oscillating crystal, is given by:

$$\Delta f = \frac{2.3 \times 10^{-6}}{A} \cdot Fo^2 \cdot Am \quad (2)$$

where $\Delta f$ is the change in frequency, $F_o$ is the fundamental frequency applied to the crystal, $\Delta m$ is the change in mass of the detection surface caused by formed non-volatile residue, and A is the area of the detection surface (typically on the order of 1 cm$^2$). This can be summarized by $$\Delta f = -K \cdot Am \quad (3)$$

where K is a constant ($K = 2.3 \times 10^{-6} F_o^2 / A$). The resonant frequency as a function of time (f(t)) can be expressed as $$f(t) = F_o - K \cdot M(t) \quad (4)$$

Accordingly, the variation in the mass over time (M(t)) can be expressed in terms of the resonant frequency Accordingly, the variation in the mass over time (M(t)) can be expressed in terms of the resonant frequency $$M(t) = \frac{fo - f(t)}{K} \quad (5)$$

Therefore, under ideal conditions changes in frequency are proportional to the change in mass of the detection surface. Such piezoelectric sensors are useful, at least in part, because of their small size and low detection limits (the lowest detection level is generally in the ppb region, with linearity to ppm). Low-level detection sensitivity is especially important in an environment in which low levels of molecular contamination are severely detrimental (e.g., in a semiconductor device fabrication area or a work environment that may be subject to gas-phase contaminants that are corrosive or toxic at low concentration levels). Such detectors should typically be replaced after a period of about six months to one year, depending on the molecular contamination concentration exposure level.

Referring to FIGS. 18B and 18C, the measured beat frequency of detector 1200 changes over time as non-volatile residues form on surface 1202. The rate of change in the beat frequency provides a measure of the rate of change in the formed mass over time ($\Delta m$).

An effective efficiency ($E_{eff}(t)$) may be determined by measuring the resonant frequency f(t) in FIG. 18A to determine the amount of non-volatile residue that has formed on a detection surface and by using equation (6), below.

$$E_{eff}(t) = \frac{M_{upstream}(t) - M_{downstream}(t)}{M_{upstream}(t)}, \quad (6)$$

An alternative measure of effective efficiency may be determined from the measured rate of change of the resonant frequency ($\Delta f$; FIG. 18B) and by using equation (7), below.

$$E'_{eff}(t) = \frac{\Delta M_{upstream}(t) - \Delta M_{downstream}(t)}{\Delta M_{upstream}(t)} \quad (7)$$

In all of the following detectors a membrane is used to control exposure of the collecting media to the molecular contamination and makes possible quantitative measurements. The collecting media (e.g., activated carbon, reagent solution, or water) varies, depending on the kind of molecular contamination that is to be monitored.

For monitoring volatile organic contaminants, such as toluene, benzene, and vapors of other low boiling point solvents, a detector 1200 (e.g., an Organic Vapor Monitor available from 3M Company of St. Paul, Minn., under the Brand Nos. 3500, 3510, 3520, and 3530, and described in H. C. Shields et al., "Analysis of ambient concentrations of organic vapors with a passive sampler," APCA Journal, Vol. 37, No. 9, (September 1987), wherein is herein incorporated by reference), may be used as upstream detector or downstream detector.

Figure 19A:
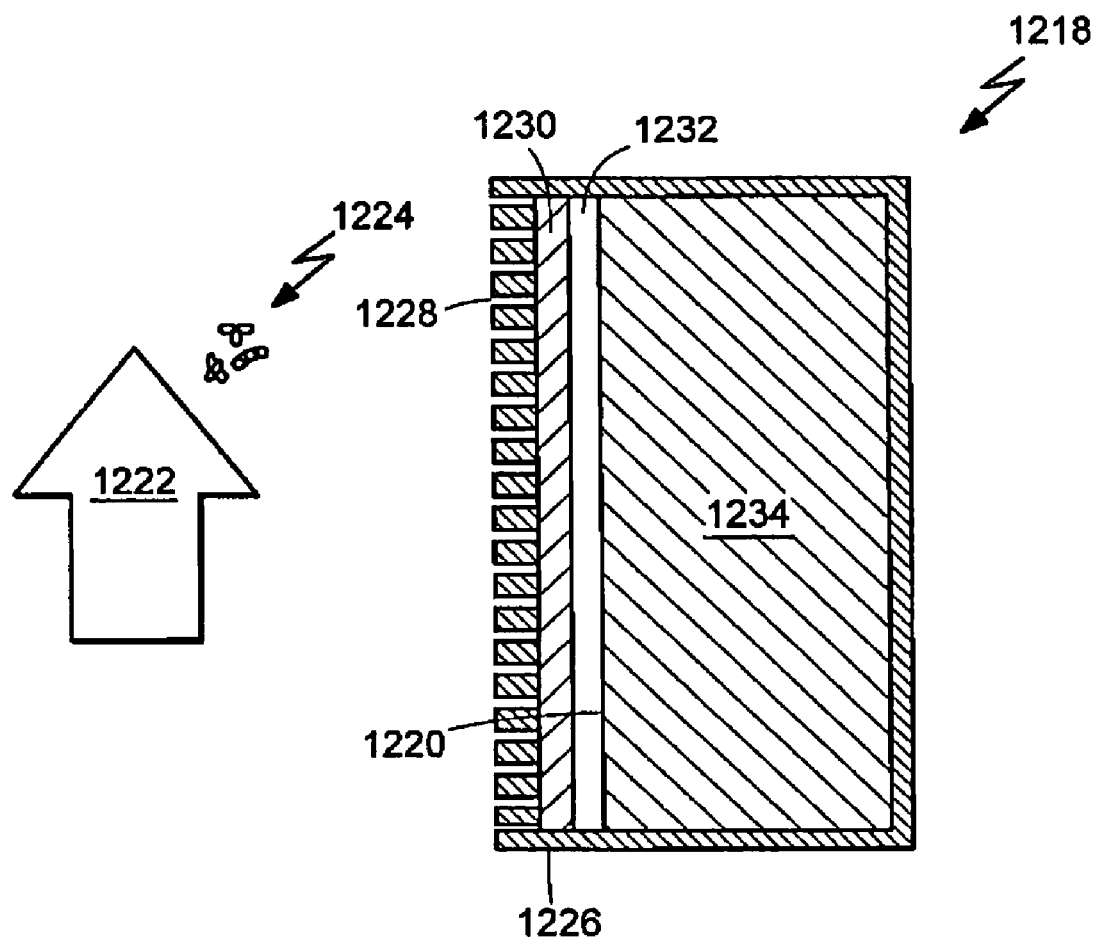
FIGS. 19A and 19B illustrate alternative embodiments of detectors for monitoring gas supplies.

Referring to FIG. 19A, detector 1213 includes a detection surface 1220, which is exposed to an incoming air stream 2004 including molecular contamination 1224 through a housing 1226 with a perforated face 1228 and through a diffusion barrier 1230 (e.g., a precalibrated semi-permeable membrane). Detector 1213 also includes a spacer 1232, and a charcoal sorbent pad 1239. The diffusion barrier creates a concentration gradient from its surface to the carbon sorbent pad.

In use, detectors are respectively positioned upstream or downstream of a filter to be monitor and left in place for a preselected period of time (t). After the preselected period, the detectors are sealed and typically taken to a lab for extraction of the adsorbed species. The pad is immersed in a solvent containing, for example, 1 µL of a 1.0 mg/mL cyclooctane/carbon disulfide solution. After a preselected period, the extract is decanted into a vial and reduced at ambient temperature and pressure in a low velocity fume hood. the final volume typically ranges from 0.5 mL to 5 1 µL. Sample volumes of 1-3 µL are injected into a gas chromatograph/mass spectrometer (e.g., a Hewlett-Packard 5992A GC/MS), which separates and identifies the adsorbed species. The identity of the molecular contamination and the collected masses of the respective components are used to calculate the concentration of the molecular contamination.

Molecular contamination 1224 contacts the detection surface of monitor 1213 by diffusion. At the surface of the screen the molecular contamination concentration is the air concentration (C) and at the sorbent pad the concentration is effectively zero. From Frick's First Law of Diffusion, it can be determined that $$C = \frac{m}{t \cdot u \cdot r} \quad (8)$$

where C is the molecular contamination concentration, m is the mass of substance adsorbed onto the sorbent pad, t is the sampling interval, u is the uptake rate, and r is the recovery coefficient (a factor used to adjust for incomplete extraction of a substance from the sorbent pad). The uptake rate (u) and the recovery rate (r) have been measured and published for a large number of organic vapors (e.g., 3M #3500 Organic Vapor Monitor Sampling Guide (Occupational Health and Safety Products Division/3M; December 1992) and 3M #3500 Organic Vapor Monitor Analysis Guide (Occupational Health and Safety Products Division/3M; 1981), both of which are herein incorporated by reference).

A filter monitor useful for monitoring formaldehyde has a similar construction as detector 1213, except the adsorbent material is coated with a solution reactive with formaldehyde (e.g., an organic passive monitor available from Advanced Chemical Sensors Co. 4901 North Dixie Hwy. Boca Raton, Fla. 33431). Formaldehyde contamination in an air stream passes through a diffusion barrier and forms a non-volatile residue on the adsorbent material. The mass of formaldehyde formed on the adsorbent material may then be measured after a preselected exposure period in a manner similar to that described above in connection with the 3M filter monitor.

Figure 19B:
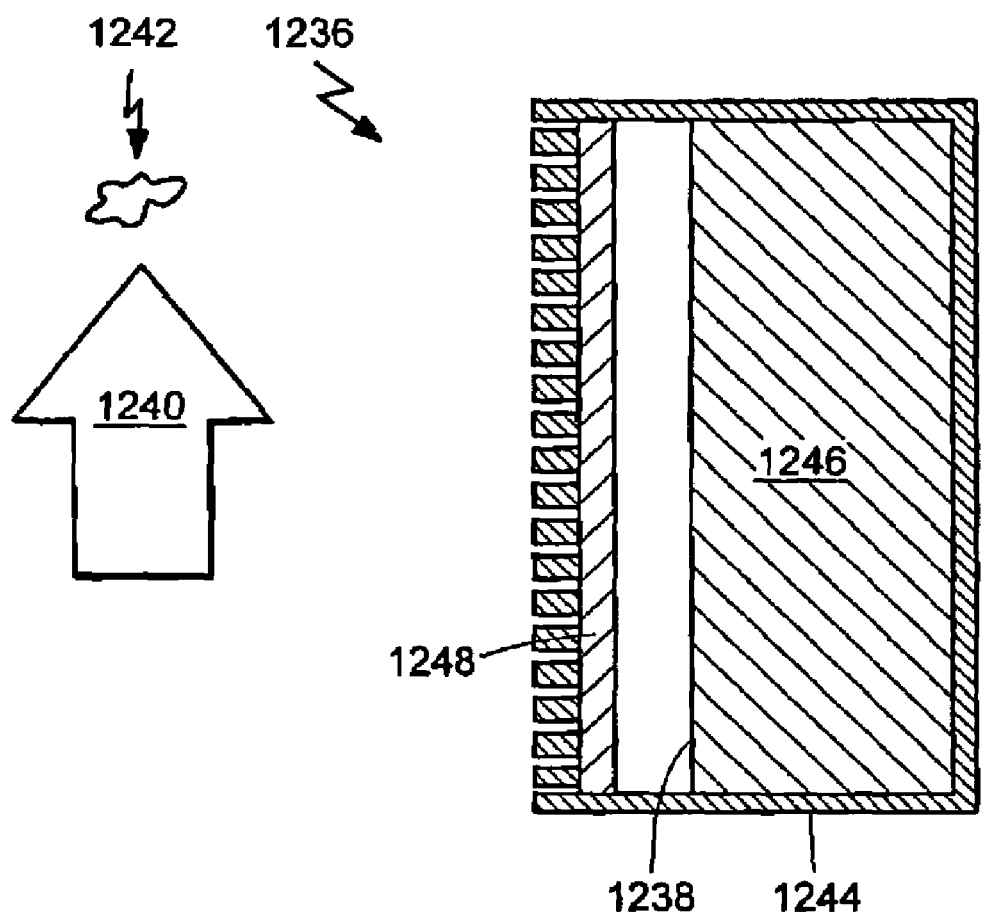

Referring to FIG. 19B, a detector 1236, which may be used as an upstream detector, mid-stack detector, or downstream detector, includes a detection surface 1238, which is exposed to an incoming air stream 1240 including molecular contamination 1242. Detector 1236 includes a housing 1244 containing adsorbent media 1246 (e.g., activated carbon particles with or without a reagent) and a diffusion barrier 1248 that creates a diffusion gradient between the air stream and the adsorbent media. The adsorbent media is the same as that used in the gas-phase filter to be monitored. In this way detector 1236 adsorbs the same gas-phase contamination as the filter with a similar sensitivity. This provides a highly accurate determination of the filter's performance. The adsorbed contamination is extracted in the same way as described above in connection with other adsorbent detectors. Embodiments of detectors for performing performance monitoring of air filters are further described in U.S. Pat. No. 5,856,198 entitled Performance Monitoring of Gas Phase Air Filters, the contents of which are herein incorporated by reference.

Figure 20:
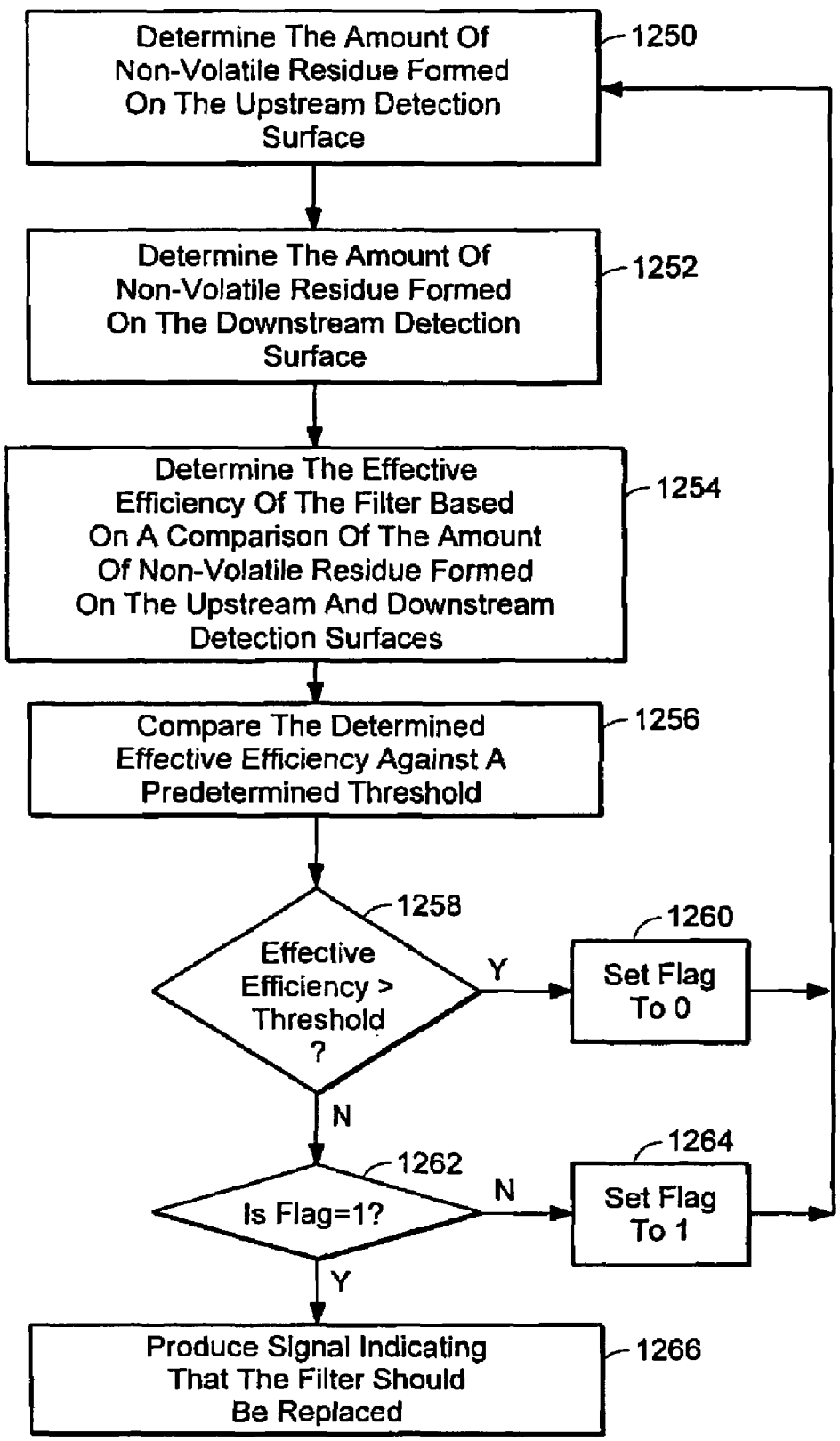
FIG. 20 illustrates a flow diagram illustrating an exemplary method of using a detector to monitor contaminants in a gas supply.

Referring to FIG. 20, in a presently preferred embodiment, the performance of a gas-phase filter is monitored as follows. The amount of non-volatile residue formed on the upstream detection surface is determined (per step 1250). The amount of non-volatile residue formed on the downstream detection surface is determined (per step 1252). The effective efficiency is determined based on a comparison of the amount of non-volatile residue formed on the upstream and downstream detection surfaces (per step 1254). The determined effective efficiency is compared against a predetermined threshold (per step 1256). If the effective efficiency is greater than the threshold (per step 1258), a flag variable is set to 0 (per step 1260) and the monitoring process is repeated. If the effective efficiency is less than the threshold and the flag variable is currently not equal to 1 (per step 1262), the flag is set to one and the monitoring process is repeated (per step 1264). If, on the other hand, the effective efficiency is less than the threshold the flag variable is equal to 1 (per step 1262), then a signal is produced indicating that the filter should be replaced (per step 1266).

In an alternative embodiment, the flag variable may be compared against an integer greater than 1 (per step 1262) and the flag variable may be increased incrementally (per step 1264) to enhance the accuracy of verification procedure (per steps 1258-1264) before the filter replacement signal is produced (per step 1266).

Figure 21:
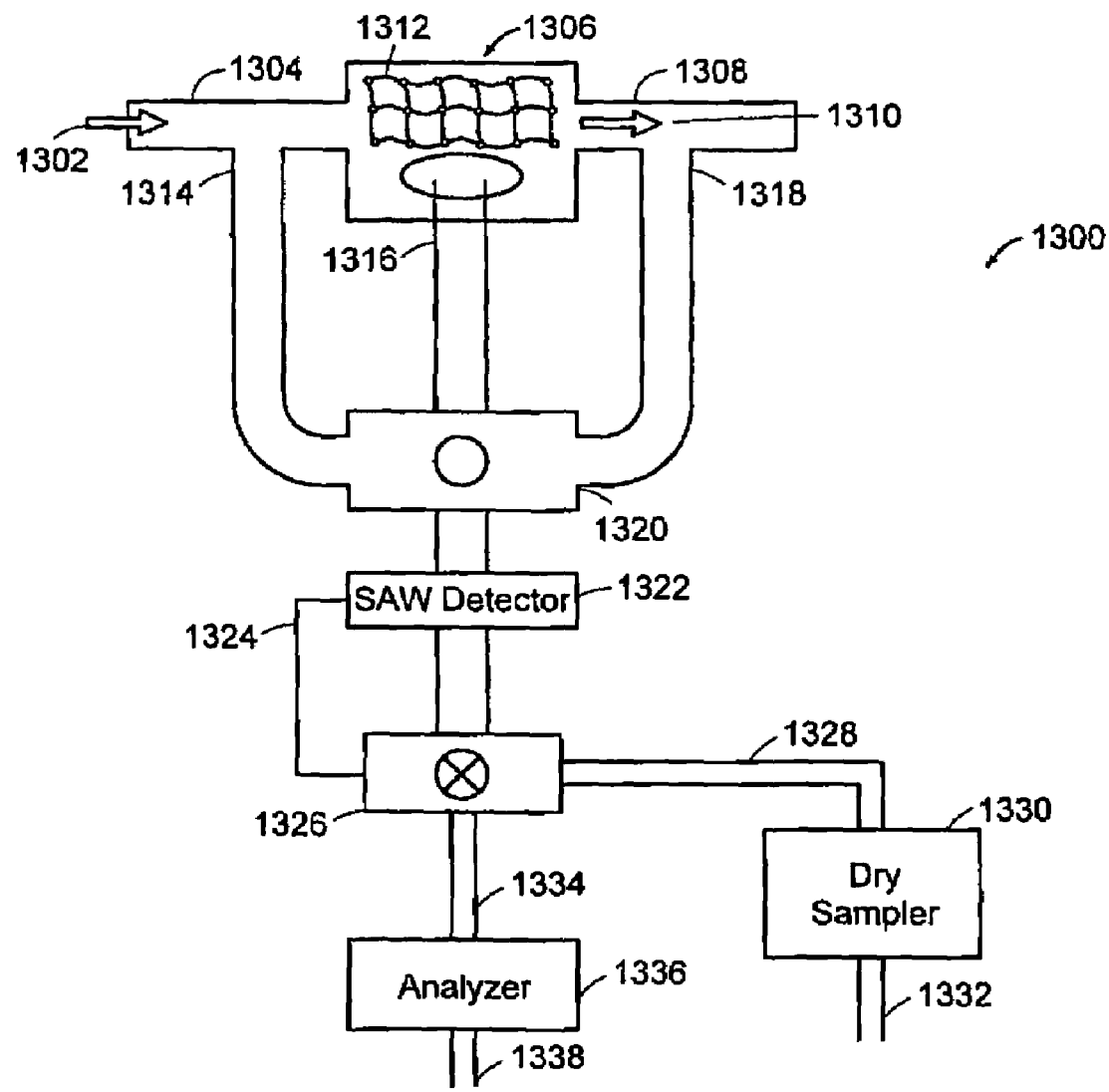
FIG. 21 illustrates an exemplary system for monitoring contaminants.

FIG. 21 illustrates a schematic representation of a system 1300 for monitoring contaminants in a reactive gas using, among other things, a surface acoustic wave (SAW) detector. System 1300 includes an inlet 1304, a chamber 1306 containing a media 1312, an outlet 1308, an inlet sample port 1314, a mid-stack sample port 1316, an outlet sample port 1318, a sample manifold 1320, a SAW detector 1322, a detector manifold 1326, a detector control line 1324, a dry sampler 1330, a dry sampler input line 1328, a dry sampler output line 1332, an analyzer 1336, an analyzer input line 1334 and an analyzer output line 1338.

An input gas sample 1302 passes through inlet 1304 and into chamber 1306. Contaminants present in gas sample 1302 are removed using media 1312 to produce an outlet gas sample 1310. A sample manifold 1320 may route a portion of a gas to SAW detector 1322 using inlet sample port 1314, mid-stack sample port 1316 or outlet sample port 1318. SAW detector 1322 may accumulate contaminants on a surface of the detector. As contaminants build up, an output signal associated with SAW detector 1322 will change. When contaminant levels on the surface of SAW detector 1322 reach or exceed a determined threshold, detector manifold 1326 may be activated, or controlled, by detector control line 1324.

When activated, detector manifold 1326 may allow a gas sample to pass through analyzer line 1334 before entering analyzer 1336. Analyzer 1336 may be a gas chromatograph or other analysis tool capable of determining a contaminant present in the gas sample. Analyzer 1336 may have an output line 1338 for exhausting the gas sample.

Detector manifold 1326 may route the gas sample through dry sampler input line 1328 to dry sampler 1330. Dry sampler 1330 may include any combination of dry traps, Tenax traps, wet impingers, and/or SAW detectors 1322 for collecting and measuring contaminants in the gas sample. Dry sampler 1330 may include an outlet 1332 for exhausting a gas sampler after passing through dry sampler 1330.

The detector can be used to initiate sampler system operation, or alternatively can be used to terminate sampler operation and indicate to the user that the sampler contents are ready to be analyzed.

In view of the wide variety of embodiments to which the principles of the present invention can be applied, it should be understood that the illustrated embodiments are exemplary only, and should not be taken as limiting the scope of the present invention. The claims should not be read as limited to the described order or elements unless stated to that effect. Therefore, all embodiments that come within the scope and spirit of the following claims and equivalents thereto are claimed as the invention.

What is claimed:

1. A method for detecting contaminants in a gas flow in a semiconductor processing facility, using a gas sampling unit, said method comprising the steps of:
    providing a gas sampling unit comprising
        an entry manifold for dividing said gas flow into at least a first sample flow and a second sample flow;
        an exit manifold having an input end for receiving said at least the first sample flow and the second sample flow after passing through a plurality of sampling devices, and an output end,
        wherein the plurality of sampling devices comprises a first dry sampling device and a second sampling device;
        a first wet impinger having an input coupled to at least the first or the second sample flow on the entry manifold, said first wet impinger further having an output; and
        a second wet impinger having an input coupled to said output of said first wet impinger and further having an output coupled to the exit manifold;
    receiving a gas flow associated with a semiconductor processing tool, the gas flow containing at least one contaminant;
    dividing said gas flow into a first sample flow and a second sample flow;
    passing said first sample flow through a first dry sampling device for detecting said contaminant;
    passing the second sample flow through a second sampling device; and
    determining a contaminant within the gas flow.

2. The method of claim 1 wherein the method further comprises:
    passing at least one sample flow through a first trap for trapping a contaminant including a condensable compound, or an organic compound or a refractory compound.

3. The method of claim 1 further comprising:
    passing said first sample flow and said second sample flow through a first dry trap and a first fibrous media trap, respectively, followed by receiving said first sample flow and second sample flow by the input end of the exit manifold.

4. The method of claim 3 wherein said gas sampling unit further comprises:
    a second dry trap for receiving a third sample flow from the entry manifold, said second dry trap further coupled to said exit manifold for facilitating passage of said third sample flow therethrough; and
    a second fibrous media trap for receiving a fourth sample flow from said entry manifold, said second fibrous media trap further coupled to said exit manifold for facilitating passage of said fourth sample flow therethrough.

5. The method of claim 1 wherein said gas sampling unit further comprises:
    a pump coupled to said unit, said pump causing said at least first sample flow and said second sample flow to pass through said sampling devices.

6. The method of claim 1 wherein said first wet impinger and said second wet impinger are used to produce a result indicative of the difference between a measured value of NO, in said first wet impinger and a measured value of NO, in said second wet impinger, said difference representing an amount of ionic NO, present in said gas flow.

7. The method of claim 6 wherein said first sampling device contains a dry collection material selected from the group consisting of acid treated quartz fibrous media, ion exchange resin, zeolites, silica gel, and acid treated pad.

8. The method of claim 1 wherein said gas sampling unit further comprises a controller.

9. The, method of claim 1 further comprising:
    shipping said gas sampling unit to an analysis facility after a sampling interval.

10. The method of claim 1 further comprising connecting said gas sampling unit to a communications network.

11. A system for measuring a contaminant in a gas flow associated with a semiconductor processing tool, said system comprising:
    an input in fluid communication with said gas flow associated with a semiconductor processing tool;
    a plurality of sampling devices, said plurality of sampling devices comprising a first dry sampling device and a second sampling devices, each said sampling device comprising an input end coupled to the input and an output port;
    an exit manifold having an input end in fluid communication with at least the first dry sampling device and the second sampling device;
    a vacuum pump coupled to an exit manifold output port for causing said gas flow to pass through said first dry sampling device;
    a pressure regulator coupled to said exit manifold, said pressure regulator for maintaining a determined pressure of said gas flow within said system; and
    a collection media that retains a contaminant removed from the gas flow.

12. The system of claim 11 further comprising:
a first fibrous media trap comprising:
an input end coupled to an entry manifold output port that receives said gas flow; and
a trap collection media for retaining contaminants.

13. The system of claim 11 further comprising:
a first bypass/purge valve; and
a second bypass/purge valve, said first and second bypass/purge valves operating cooperatively for allowing said gas flow to bypass an entry manifold when said valves are in a bypass position, respectively, and for allowing said gas flow to pass through said entry manifold when said valves are in a run position, respectively.

14. The system of claim 11 further comprising: a controller for controlling operation of said system.

15. The system of claim 11 further comprising: a network interface for communicatively coupling said system to a network.

16. The system of claim 11 further comprising a housing in which the system is housed.

17. The system of claim 11 further comprising:
a first wet impinger having an input coupled to a third one of a plurality of entry manifold output ports and further having a first wet impinger output port; and
a second wet impinger having an input coupled to said output of said first wet impinger and further having a second wet impinger output coupled to said exit manifold.

18. The method of claim 17 wherein said first wet impinger and said second wet impinger contain deionized water.

19. The system of claim 18 further comprising:
a second dry trap; and a second fibrous media trap.

20. The system of claim 11 wherein said first wet impinger and said second wet impinger are used to produce a result indicative of the difference between a measured value of ionic $NO_x$ in said first wet impinger and a measured value of ionic $NO_x$ in said second wet impinger, said difference representing the actual amount of atmospheric ionic $NO_x$ present in a sample of said gas flow.

21. The system of claim 11 wherein said first sampling device includes a dry collection media selected from the group consisting of acid treated quartz fibrous media, ion exchange resin, zeolites, silica gel, and acid treated media.

22. The system of claim 11 further comprising:
a detector having an output signal that changes in response to the presence of at least one of said contaminants on a surface of said detector.

23. The system of claim 22 wherein said surface has a coating to facilitate retention of said at least one of said contaminants.

24. The system of claim 22 wherein the detector is an acoustic detector.

25. The system of claim 11 further comprising a detector that initiates operation of the first dry sampling device.

26. The system of claim 11 further comprising a detector that terminates operation of the sampler.

27. The system of claim 11 wherein the system comprises a handheld device having a display.

28. The system of claim 11 further comprising a trap module that is removeably inserted into a system housing.

29. The system of claim 28 wherein the trap module includes an acid trap, a base trap and an organic compound trap.

30. The system of claim 11 further comprising a valve system and a controller connected to the valve system to automatically control gas flow within the system.

31. A method for detecting contaminants in a gas flow in a cleanroom environment, using a gas sampling unit, said method comprising the steps of:
receiving a gas flow containing at least one contaminant at an entry manifold;
dividing said gas flow into a first sample flow and a second sample flow;
passing said first sample flow through a first wet impinger sampling device for detecting said contaminant to an exit manifold;
passing the second sample flow through a second sampling device to the exit manifold; and
determining a contaminant within the gas flow.

32. The method of claim 31 wherein said method further comprises: passing said second sample flow through a first fibrous media trap for detecting a contaminant.

33. The method of claim 31 wherein said gas sampling method further comprises providing:
the exit manifold, the exit manifold having an input end for receiving said first sample flow and said second sample flow after passing through a first dry trap and a further sample flow after passing through a first fibrous media trap, respectively, said exit manifold further having an output end.

34. The method of claim 33 wherein said gas sampling method further comprises:
a second dry trap for receiving a third sample flow from the entry manifold, said second dry trap further coupled to said exit manifold for facilitating passage of said third sample flow therethrough; and
a second fibrous media sample flow trap for receiving a fourth sample flow from said entry manifold, said second fibrous media trap further coupled to said exit manifold for facilitating passage of fourth sample flow therethrough.

35. The method of claim 31 wherein said gas sampling method further comprises providing:
a pump coupled to said unit, said pump causing said first sample flow and said second sample flow to pass through said sampling devices.

36. The method of claim 31 further comprising using said first wet impinger and a second wet impinger to produce a result indicative of the difference between a measured value of NO, in said first wet impinger and a measured value of NO, in said second wet impinger, said difference representing an amount of ionic NO, present in said gas flow.

37. The method of claim 31 wherein said gas sampling method further comprises providing a controller.

38. The method of claim 31 further comprising providing a first dry sampling device with a dry collection material selected from the group consisting of acid treated quartz fibrous media, ion exchange resin, zeolites, silica gel, and acid treated media.

* * * * *